United States Patent

Nakazato et al.

Patent Number: 5,495,046
Date of Patent: Feb. 27, 1996

[54] ALKOXYPHENYLALKYLAMINE DERIVATIVES

[75] Inventors: Atsuro Nakazato; Yoshinori Sekiguchi; Koumei Ohta; Yutaka Kawashima; Katsuo Hatayama, all of Tokyo, Japan

[73] Assignee: Taisho Pharmaceutical Co., Ltd., Japan

[21] Appl. No.: 211,449

[22] PCT Filed: Sep. 30, 1992

[86] PCT No.: PCT/JP92/01259

§ 371 Date: Mar. 31, 1994

§ 102(e) Date: Mar. 31, 1994

[87] PCT Pub. No.: WO93/07113

PCT Pub. Date: Apr. 15, 1993

[30] Foreign Application Priority Data

| Oct. 4, 1991 | [JP] | Japan | 3-256844 |
| Oct. 4, 1991 | [JP] | Japan | 3-257274 |
| Oct. 4, 1991 | [JP] | Japan | 3-257292 |

[51] Int. Cl.⁶ .......... C07C 217/56; C07C 217/86; C07C 217/62
[52] U.S. Cl. .............. 562/597; 564/5
[58] Field of Search .......... 562/597, 405, 562/442; 514/239.2, 237.5; 564/5

[56] References Cited

U.S. PATENT DOCUMENTS

| 4,329,367 | 11/1982 | Francis | 424/330 |
| 5,086,054 | 2/1992 | Parish | 514/239.2 |

FOREIGN PATENT DOCUMENTS

| 0418430 | 9/1989 | European Pat. Off. | C07D 317/64 |
| 0365064 | 4/1990 | European Pat. Off. | |
| 2-179 | 1/1990 | Japan | |
| 2-49726 | 2/1990 | Japan | |
| 249726 | 2/1990 | Japan | A61K 31/44 |
| 2088873 | 6/1982 | United Kingdom | |
| 9011997 | 10/1990 | WIPO | |

*Primary Examiner*—Arthur C. Prescott
*Attorney, Agent, or Firm*—Lorusso & Loud

[57] ABSTRACT

An alkoxyphenylalkylamine derivative represented by the following formula:

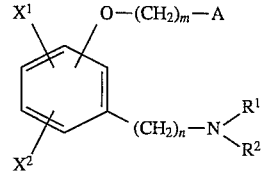

(wherein $X^1$ and $X^2$ may be either the same or different from each other and each represents a hydrogen atom, a halogen atom, a hydroxyl group, an alkoxy group having 1 to 5 carbon atoms or an alkoxy group having 1 to 5 carbon atoms and substituted with a phenyl group; $R^1$ and $R^2$ may be either the same or different from each other and each represents a hydrogen atom, an alkyl group having 1 to 7 carbon atoms, an alkyl group having 1 to 7 carbon atoms and substituted with "a hydroxyl group, a carboxyl group or an alkoxycarbonyl group" at the end, or, $R^1$ and $R^2$ together with the adjacent nitrogen atom represent a pyrrolidino group, a piperidino group or a piperadino group, all of which may be optionally substituted; A represents a phenyl group, a phenyl group substituted with 1 to 3 substituents arbitrarily selected from "a halogen atom, a hydroxyl group and an alkoxy group having 1 to 5 carbon atoms" or a thienyl group; m is an integer of from 2 to 5; and n is an integer of from 2 to 7), and a salt thereof.

3 Claims, No Drawings

ALKOXYPHENYLALKYLAMINE DERIVATIVES

CROSS-REFERENCE TO RELATED APPLICATION

The present application was filed under the provisions of 35 usc 371(c) as the U.S. National Phase of PCT application PCT/JP92/10259 filed Sep. 30, 1992.

TECHNICAL FIELD

This invention relates to alkoxyphenylalkylamine derivatives having an antipsychotic action.

BACKGROUND ART

Antipsychotic drugs are used for treating not only schizophrenia but also troublesome behaviors (for example, aggression, mental excitation, fugue, delirium) accompanying cerebrovascular disorders and senile dementia. However, there is a serious problem that these classical antipsychotic drugs cause extrapyramidal disorders as a side effect. In order to solve this problem, approaches have been made in recent years to develop antipsychotic drugs from a viewpoint which is completely different from the action mechanism of the classical drugs. As an example of these approaches, a sigma receptor antagonist may be cited. It is considered that sigma receptor is a receptor participating in mental abnormality such as hallucination. A compound having a specific affinity for this receptor would exhibit an antipsychotic action without causing any extrapyramidal disorders.

Although Rimcazole is known as an example of such a compound, its affinity and specificity for sigma receptor are restricted.

There have been known some compounds, for example, N,N-dimethyl-2-(3-benzyloxy-4-methoxy-phenyl)ethylamine described in J. C. S. Perkin I, (1975), page 1140, which are similar to the compound of the present invention in structure. However, these compounds are described merely as a synthesis intermediate. Thus the action of the compound of the present invention has never been reported hitherto.

It is an object of the present invention to provide a novel compound which has an antipsychotic action without causing any extrapyramidal disorders.

DISCLOSURE OF THE INVENTION

The present inventors have conducted extensive studies on alkoxyphenylalkylamine derivatives. As a result, they have found out a novel alkoxyphenylalkylamine derivative which shows a specific and high affinity for sigma receptor, thus completing the present invention.

Now the present invention will be described in greater detail.

The present invention relates to an alkoxyphenylalkylamine derivative represented by the following formula (I):

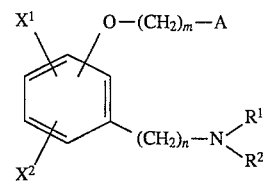

(wherein $X^1$ and $X^2$ may be either the same or different from each other and each represents a hydrogen atom, a halogen atom, a hydroxyl group or an alkoxy group having 1 to 5 carbon atoms, which may be substituted with a phenyl group; $R^1$ and $R^2$ may be either the same or different from each other and each represents a hydrogen atom or an alkyl group having 1 to 7 carbon atoms, which may be substituted with "a hydroxyl group, a carboxyl group or an alkoxycarbonyl group" at the end, or, $R^1$ and $R^2$ together with the adjacent nitrogen atom represent a pyrrolidino group, a piperidino group, a homopiperidino group, a morpholino group, a piperazino group, a homopiperazino group or a piperazino group substituted with "a phenyl group, a phenyl group substituted with a lower alkyl group or a lower alkoxy group, a pyridyl group, a pyridyl group substituted with a lower alkyl group or a lower alkoxy group, a pyrimidyl group or a pyrimidyl group substituted with a lower alkyl group or a lower alkoxy group"; A represents a phenyl group, a phenyl group substituted with 1 to 3 substituents arbitrarily selected from "a halogen atom, a hydroxyl group and an alkoxy group having 1 to 5 carbon atoms", or a thienyl group; m is an integer of from 2 to 5; and n is an integer of from 2 to 7), and a salt thereof.

In further aspects, the present invention relates to the followings:

an alkoxyphenylalkylamine derivative represented by the following formula:

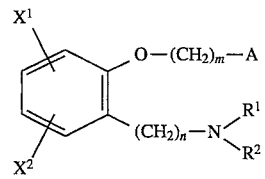

wherein $X^1$ and $X^2$ may be either the same or different from each other and each represents a hydrogen atom, a halogen atom or an alkoxy group having 1 to 5 carbon atoms; $R^1$ and $R^2$ may be either the same or different from each other and each represents a hydrogen atom or an alkyl group having 1 to 7 carbon atoms, or, $R^1$ and $R^2$ together with the adjacent nitrogen atom represent a pyrrolidino group, a piperidino group, a homopiperidino group, a morpholino group, a piperazino group, a homopiperazino group or a piperazino group substituted with a substituent selected from the group consisting of a phenyl group, a phenyl group substituted with a lower alkyl group or a lower alkoxy group, a pyridyl group and a pyrimidyl group substituted with a lower alkyl group or a lower alkoxy group; A represents a phenyl group or a phenyl group substituted with 1 to 3 substituents selected from the group consisting of a halogen atom, a hydroxyl group and an alkoxy group having 1 to 5 carbon atoms; m is an integer of from 2 to 5; and n is an integer of from 2 to 7, and a salt thereof;

an alkoxyphenylalkylamine derivative represented by the following formula:

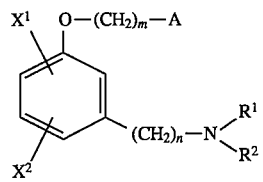

wherein $X^1$ and $X^2$ may be either the same or different from each other and each represents a hydrogen atom, a hydroxyl group, an alkoxy group having 1 to 5 carbon atoms or an alkoxy group having 1 to 5 carbon atoms and substituted with a phenyl group; $R^1$ and $R^2$ may be either the same or different from each other and each represents a hydrogen atom, an alkyl group having 1 to 7 carbon atoms or an alkyl group having 1 to 7 carbon atoms and substituted with a substituent selected from the group consisting of a hydroxyl group, a carboxyl group and an alkoxycarbonyl group at the end, or, $R^1$ and $R^2$ together with the adjacent nitrogen atom represent a pyrrolidino group, a piperidino group, a homopiperidino group, a morpholino group, a piperazino group, a homopiperazino group or a piperazino group substituted with a substituent selected from the group consisting of a phenyl group, a phenyl group substituted with a lower alkyl group or a lower alkoxy group, a pyridyl group, a pyridyl group substituted with a lower alkyl group or a lower alkoxy group, a pyrimidyl group and a pyrimidyl group substituted with a lower alkyl group or a lower alkoxy group; A represents a phenyl group, a phenyl group substituted with 1 to 3 substituents selected from the group consisting of a halogen atom, a hydroxyl group and an alkoxy group having 1 to 5 carbon atoms, or a thienyl group; m is an integer of from 2 to 5; and n is an integer of from 2 to 7, and a salt thereof;

an alkoxyphenylalkylamine derivative represented by the following formula:

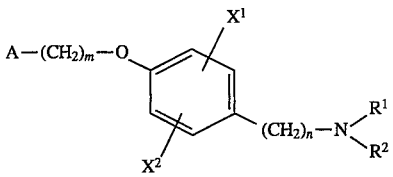

wherein $X^1$ and $X^2$ may be either the same or different from each other and each represents a hydrogen atom, a hydroxyl group, an alkoxy group having 1 to 5 carbon atoms or an alkoxy group having 1 to 5 carbon atoms and substituted with a phenyl group; $R^1$ and $R^2$ may be either the same or different from each other and each represents a hydrogen atom or an alkyl group having 1 to 7 carbon atoms, or, $R^1$ and $R^2$ together with the adjacent nitrogen atom represent a pyrrolidino group, a piperidino group, a homopiperidino group, a morpholino group, a piperazino group, a homopiperazino group or a piperazino group substituted with a substituent selected from the group consisting of a phenyl group, a phenyl group substituted with a lower alkyl group or a lower alkoxy group, a pyridyl group, a pyridyl group substituted with a lower alkyl group or a lower alkoxy group, a pyrimidyl group and a pyrimidyl group substituted with a lower alkyl group or a lower alkoxy group; A represents a phenyl group or a phenyl group substituted with 1 to 3 substituents selected from the group consisting of a halogen atom, a hydroxyl group and an alkoxy group having 1 to 5 carbon atoms; m is an integer of from 2 to 5; and n is an integer of from 2 to 7, and a salt thereof;

an alkoxyphenylalkylamine derivative represented by the following formula:

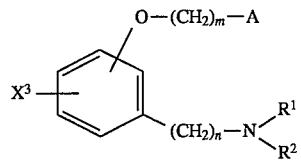

wherein $X^3$ represents a hydrogen atom, a halogen atom, a hydroxyl group or an alkoxy group having 1 to 5 carbon atoms; $R^1$ and $R^2$ may be either the same or different from each other and each represents a hydrogen atom or an alkyl group having 1 to 7 carbon atoms, or, $R^1$ and $R^2$ together with the adjacent nitrogen atom represent a pyrrolidino group, a piperidino group, a homopiperidino group, a morpholino group, a piperazino group, or a piperazino group substituted with a substituent selected from the group consisting of a phenyl group, a phenyl group substituted with a lower alkyl group or a lower alkoxy group, a pyridyl group, a pyridyl group substituted with a lower alkyl group or a lower alkoxy group, a pyrimidyl group and a pyrimidyl group substituted with a lower alkyl group or a lower alkoxy group; A represents a phenyl group or a phenyl group substituted with 1 to 3 substituents selected from the group consisting of a halogen atom, a hydroxyl group and an alkoxy group having 1 to 5 carbon atoms; m is an integer of from 2 to 5; and n is an integer of from 2 to 7, and a salt thereof; or an alkoxyphenylalkylamine derivative represented by the following formula:

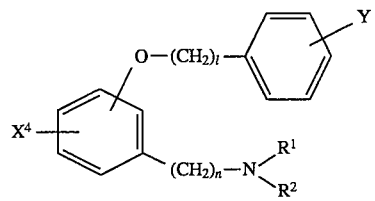

wherein $X^4$ represents a hydrogen atom, a halogen atom, a hydroxyl group or a methoxy group; $R^1$ and $R^2$ may be either the same or different from each other and each represents an alkyl group having 1 to 7 carbon atoms; Y represents a hydrogen atom, a halogen atom, a hydroxyl group or a methoxy group; l is an integer of 2 or 3; and n is an integer of from 2 to 7, and a salt thereof.

Examples of the halogen atom to be used in the present invention include fluorine, chlorine, bromine and iodine atoms. The alkoxy group having 1 to 5 carbon atoms to be used herein means a linear or branched alkoxy group such as methoxy, ethoxy, propoxy, isopropoxy, butoxy, isobutoxy, tert-butoxy, pentoxy or isopentoxy group. Examples of the alkoxy group having 1 to 5 carbon atoms and substituted with a phenyl group include benzyloxy, 2-phenylethoxy and 3-phenylpropoxy groups. Examples of the alkyl group having 1 to 7 carbon atoms and substituted with "a hydroxyl group, a carboxyl group or an alkoxycarbonyl group" at the end include 3-hydroxypropyl, 2-hydroxycarbonylethyl and 2-alkoxycarbonylethyl groups (wherein alkoxy means an alkoxy group having 1 to 5 carbon atoms). The alkyl group having 1 to 7 carbon atoms means a linear or branched alkyl group such as methyl, ethyl, propyl, isopropyl, butyl, isobutyl, pentyl, isopentyl, hexyl, isohexyl, heptyl or isoheptyl group. The lower alkyl group means an alkyl group having 1 to 3 carbon atoms, while the lower alkoxy group means an alkoxy group having 1 to 3 carbon atoms. Therefore, examples of the piperazino group substituted with "a phenyl group, a phenyl group substituted with a lower alkyl group or a lower alkoxy group, a pyridyl group, a pyridyl group substituted with a lower alkyl group or a lower alkoxy group, a pyrimidyl group or a pyrimidyl group substituted with a lower alkyl group or a lower alkoxy group" include N-phenylpiperazino, N-(2-methoxyphenyl)piperazino, N-(2-pyridyl)piperazino, N-[2-(6-methyl)pyridyl] piperazino and (2-pyrimidyl)piperazino groups.

The salt of the compound of the present invention means a pharmacologically acceptable salt and examples thereof include salts with a mineral acid such as sulfuric acid, hydrochloric acid or phosphoric acid and salts with an organic acid such as acetic acid, oxalic acid, lactic acid, tartaric acid, fumaric acid, maleic acid, trifluoroacetic acid or methanesulfonic acid.

Typical examples of the compound of the present invention are as follows.

N,N-Di-n-propyl-2-[5-chloro-2-(2-phenylethoxy)phenyl] ethylamine oxalate.

N,N-Di-n-propyl-3-[5-chloro-2-(2-phenylethoxy)phenyl] propylamine oxalate.

N,N-Di-n-propyl-4-[5-chloro-2-(2-phenylethoxy)phenyl] butylamine oxalate.

N,N-Di-n-propyl-2-[4-chloro-2-(2-phenylethoxy)phenyl] ethylamine hydrochloride.

N,N-Di-n-propyl-2-[5-bromo-2-(2-phenylethoxy)phenyl] ethylamine oxalate.

N,N-Di-n-propyl-3-[5-bromo-2-(2-phenylethoxy)phenyl] propylamine oxalate.

N,N-Di-n-propyl-2-[5-fluoro-2-(2-phenylethoxy)phenyl] ethylamine hydrochloride.

N,N-Di-n-propyl-2-[3-fluoro-2-(2-phenylethoxy)phenyl] ethylamine oxalate.

N,N-Di-n-propyl-2-[4-methoxy-3-(2-phenylethoxy)phenyl] ethylamine oxalate.

N,N-Di-n-propyl-2-[4-methoxy-3-(2-phenylethoxy)phenyl] ethylamine hydrochloride.

N,N-Di-n-propyl-3-[4-methoxy-3-(2-phenylethoxy)phenyl] propylamine oxalate.

N,N-Di-n-propyl-3-[4-methoxy-3-(2-phenylethoxy)phenyl] propylamine hydrochloride.

N,N-Di-n-propyl-2-[4-methoxy-3-(3-phenylpropoxy)phenyl] ethylamine oxalate.

N-2-[4-Methoxy-3-(2-phenylethoxy)phenyl]ethyl-N'-phenylpiperazine oxalate.

N,N-Di-n-propyl-2-[4-hydroxy-3-(2-phenylethoxy)phenyl] ethylamine hydrochloride.

N,N-Di-n-propyl-2-[4-methoxy-3-[2-(4-fluorophenyl)ethoxy] phenyl]ethylamine hydrochloride.

N,N-Di-n-propyl-2-[4-methoxy-3-[2-(3-chlorophenylethoxy] phenyl]ethylamine oxalate.

N,N-Di-n-propyl-2-[4-methoxy-3-[2-(4-methoxyphenyl)ethoxy] phenyl]ethylamine oxalate.

N,N-Di-n-propyl-2-[4-methoxy-3-[2-(2-thienyl)ethoxy] phenyl] ethylamine hydrochloride.

N,N-Di-n-propyl-2-[3-methoxy-4-(2-phenylethoxy)phenyl] ethylamine oxalate.

N-n-Propyl-N-3-hydroxypropyl-2-[4-methoxy-3-(2phenylethoxy)phenyl] ethylamine oxalate.

N,N-Di-n-propyl-2-[3-methoxy-2-(2-phenylethoxy)phenyl] ethylamine oxalate.

N,N-Di-n-propyl-2-[3-methoxy-2-(2-phenylethoxy)phenyl] ethylamine hydrochloride.

N,N-Di-n-propyl-3-[3-methoxy-2-(2-phenylethoxy)phenyl] propylamine oxalate.

N,N-Di-n-propyl-2-[3-methoxy-2-(3-phenylpropoxy)phenyl] ethylamine oxalate.

N-2-[3-Methoxy-2-(2-phenylethoxy)phenyl]ethylpyrrolidine oxalate.

N,N-Di-n-propyl-2-[5-methoxy-2-(2-phenylethoxy)phenyl] ethylamine hydrochloride.

N,N-Di-n-propyl-2-[4-methoxy-2-(2-phenylethoxy)phenyl] ethylamine oxalate.

N,N-Di-n-propyl-2-[2-methoxy-4-(2-phenylethoxy)phenyl] ethylamine oxalate.

The compound of the formula (I) of the present invention can be produced by the following methods. (In the following reaction formulae, $R^3$ represents an alkyl group having 1 to 5 carbon atoms; $R^4$ represents a linear or branched alkyl group having 1 to 6 carbon atoms; $R^5$ represents a substituent of $R^1$ other than a hydrogen atom; X represents an arbitrary halogen atom; Z represents a hydrogen atom or an alkoxy group having 1 to 5 carbon atoms; and $R^1$, $R^2$, $X^1$, $X^2$, A, m and n are as defined above.)

[Route 1]

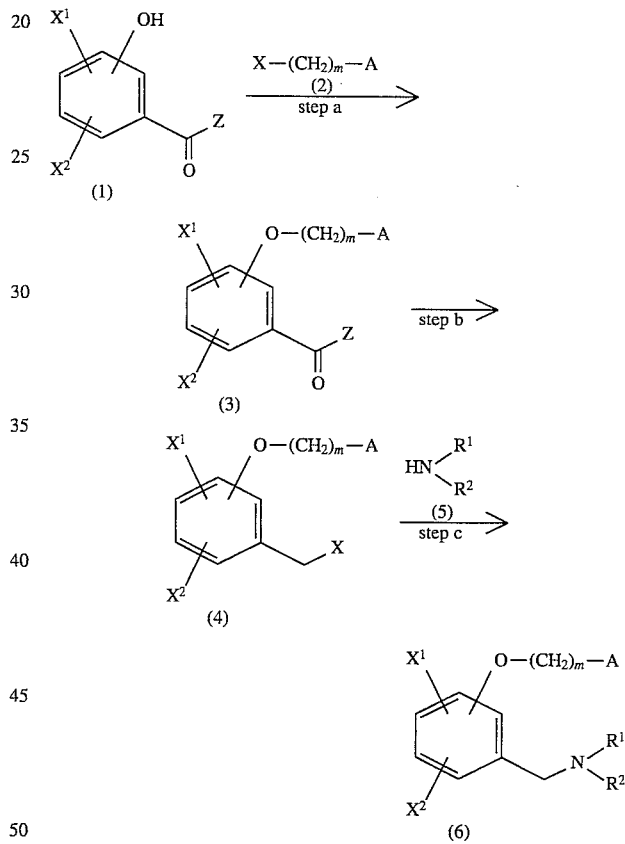

Step a: A hydroxybenzaldehyde or hydroxybenzoate of the formula (1) is reacted with a halide of the formula (2) in an inert solvent in the presence or absence of a phase-transfer catalyst and in the presence of a base to give a compound of the formula (3).

As examples of the phase-transfer catalyst usable in the present invention, a quaternary ammonium salt such as benzyltriethylammonium chloride, tetrabutylammonium bromide or trioctylmethylammonium chloride may be used. As the base, an inorganic base such as sodium carbonate, potassium carbonate, sodium hydroxide, potassium hydroxide, potassium fluoride or sodium hydride and an organic base such as triethylamine or pyridine may be used. As the inert solvent, an organic solvent such as N,N-dimethylformaldehyde, acetonitrile, dichloromethane, chloroform, tetrahydrofuran, benzene, toluene, methanol or ethanol, or a mixture of one of these organic solvents with water may be used. The reaction is carried out at from room temperature to 150° C. under stirring for 3 to 48 hours, preferably at from room temperature to 70° C. under stirring for 5 to 24 hours.

Step b: The aldehyde or ester of the formula (3) is reduced with a reducing agent in an inert solvent and then halogenated with a halogenating agent to give a compound of the formula (4).

As examples of the solvent usable in the reduction, tetrahydrofuran, diethyl ether, benzene, toluene, methanol and ethanol may be used. As the reducing agent, an aluminum-series reducing agent such as aluminum lithium hydride and a boron-series reducing agent such as sodium borohydride may be used. This reaction is carried out at 0° to 100° C. under stirring for 1 to 10 hours, preferably at 0° C. to room temperature under stirring for 1 to 5 hours.

As examples of the halogenating agent usable in the halogenation, thionyl chloride, phosphorus oxychloride, phosphorus oxybromide, phosphorus pentachloride, conc. hydrochloric acid, a solution of hydrogen bromide in acetic acid and hydroiodic acid may be used. The reaction may be performed without using any solvent. Alternately, solvents such as dichloromethane, tetrahydrofuran, benzene, toluene, N,N-dimethylformamide or hexamethylphosphorictriamide may be used therefor either alone or in the form of a mixture thereof. This reaction is carried out at 0° to 130° C. under stirring for 1 to 24 hours, preferably at room temperature to 100° C. under stirring for 2 to 10 hours.

Step c: The compound of the formula (4) is reacted with an amine of the formula (5) in the presence of a base to give a compound of the formula (6).

As examples of the base usable in this reaction, an inorganic base such as sodium carbonate or potassium carbonate, a tertiary amine such as triethylamine, diisopropylethylamine, N-methylmorpholine or N,N-dimethylaniline and the amine of the formula (5) may be used. As the solvent, acetonitrile, methanol, ethanol, isopropanol, toluene, benzene, tetrahydrofuran, dioxane and N,N-dimethylformamide may be used. This reaction is carried out at 50° to 150° C. for 5 to 48 hours, preferably at 50° to 100° C. for 8 to 48 hours, under stirring.

mide, trioctylmethylammonium chloride or benzyltriethylammonium chloride. As the solvent, acetonitrile, benzene, toluene, chloroform, dichloromethane, tetrahydrofuran, N,N-dimethylformamide, dimethylsulfoxide, acetone and methyl ethyl ketone may be used either alone or in the form of a mixture of one of these solvents with water. This reaction is carried out at room temperature to 150° C. under stirring for 3 to 24 hours.

The hydrolysis is performed with the use of a base such as sodium hydroxide, potassium hydroxide or calcium hydroxide and an acid such as hydrochloric acid, sulfuric acid or acetic acid. Examples of the solvent usable herein are a mixture of water and an organic solvent, for example, alcohols such as ethanol, ethers such as dioxane or 1,2-dimethoxyethane and N,N-dimethylformamideo This reaction is carried out under refluxing for 5 to 24 hours with stirring.

Step e: Next, the carboxylic acid of the formula (7) is converted into a mixed acid anhydride or an acid halide to activate the carboxyl group. Then the product is converted into an amide by reacting with the amine of the formula (5). After further reducing, the compound of the present invention of the formula (8) can be obtained.

In the above step, the compound of the formula (7) may be converted into a mixed acid anhydride by reacting it with, for example, ethyl chlorocarbonate, isobutyl chlorocarbonate, acetic anhydride or acetyl chloride in a solvent in the presence of a base (for example, triethylamine or N-methylmorpholine). Examples of the solvent usable herein include tetrahydrofuran, dichloromethane, N,N-dimethylformamide, toluene and benzene. On the other hand, the compound of the formula (7) may be converted into an acid halide by reacting with thionyl chloride or thionyl bromide in a solvent such as benzene, toluene, dichloromethane, chloroform or N,N-dimethylformamide, or without using any solvent.

In the reduction, a reducing agent such as aluminum lithium hydride, sodium bis(methoxyethoxy)aluminum hydride or borane-tetrahydrofuran complex and a solvent such as tetrahydrofuran, 1,2-dimethoxyethane or toluene are used. This reaction is carried out at 0° to 150° C. under stirring for 1 to 24 hours, preferably at room temperature to 80° C. under stirring for 2 to 10 hours.

[Route 2]

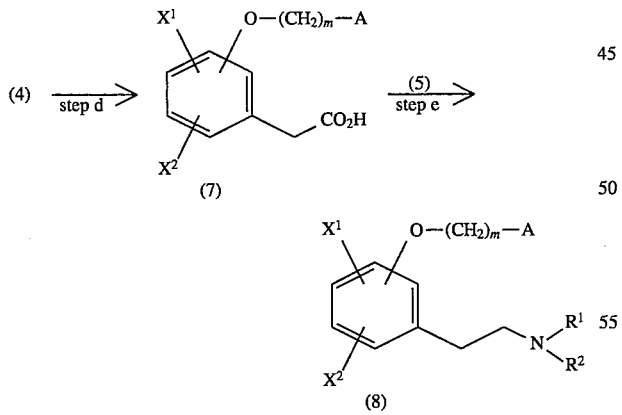

[Route 3]

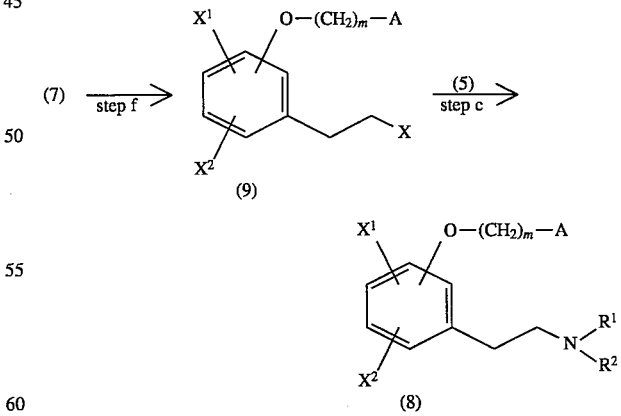

Step d: The compound of the formula (4) obtained by the route 1 is subjected successively to cyanation and hydrolysis to give a carboxylic acid of the formula (7).

In the cyanation of this step, a cyanation agent such as potassium cyanide, sodium cyanide or copper cyanide is used in the absence or presence of a catalyst. The catalyst usable herein is a phase-transfer catalyst, for example, crown ethers such as 18-crown-6, tetrabutylammonium bro- Step f: The carboxylic acid (7) obtained by the route 2 is reduced with a reducing agent and then subjected to a halogenation similar to that of the step b to obtain a halide of the formula (9).

As examples of the reducing agent usable herein, aluminum lithium hydride, sodium bis(methoxyethoxy)aluminum hydride and borane-tetrahydrofuran complex may be used. As examples of the solvent, tetrahydrofuran, 1,2-dimethoxyethane, ether, toluene or benzene may be used. This reaction is carried out at 0° to 70° C. under stirring for 1 to 8 hours.

By reacting the halide of the formula (9) with the amine of the formula (5) in the same manner as that of the step c, the compound of the formula (8) of the present invention can be obtained.

Subsequently, the halide of the formula (9) is subjected to the cyanation and hydrolysis of the step d and the reduction and halogenation of the step f. Then the halide thus obtained is reacted with the amine similar to the step c. Thus the compound of the formula (I) of the present invention, wherein the carbon atom number [represented by n in the formula (I)] has been successively increased, can be obtained.

water by using, for example, sodium hydroxide, potassium hydroxide, lithium hydroxide, calcium hydroxide, hydrochloric acid, sulfuric acid or acetic acid at room temperature to 100° C. for 1 to 36 hours, preferably at room temperature for 2 to 12 hours.

Next, the carboxylic acid of the formula (11) can be converted into the compound of the formula (12) of the present invention by treating in the same manner as that of the step e or the steps f and c.

Subsequently, the compound of the formula (I), wherein n is an arbitrary integer, can be synthesized by subjecting the carboxylic acid of the formula (11) successively to the steps f, c, d and e.

[Route 4]

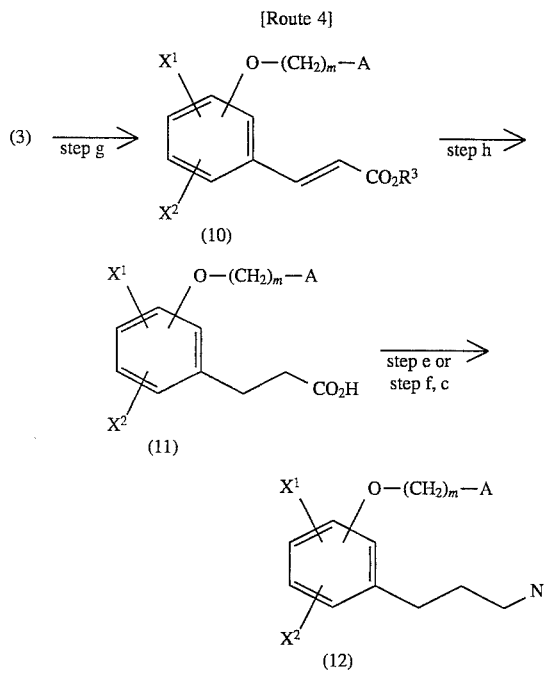

[Route 5]

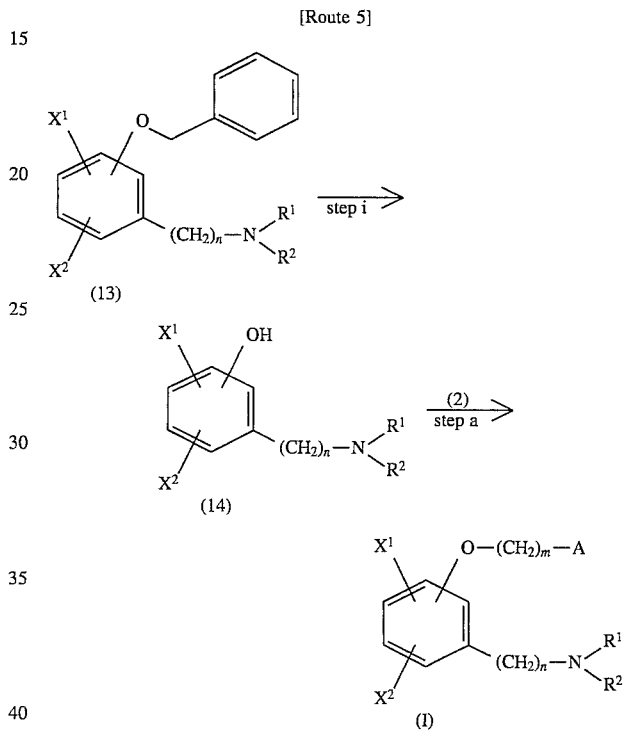

Step g: The aldehyde (Z=H) of the formula (3) obtained by the route 1 is reacted with a phosphorus ylide to give a cinnamate compound of the formula (10).

Examples of the phosphorus ylide to be used herein include an ethyl diethylphosphonoacetate anion and methyl triphenylphosphoranilideneacetate. As examples of the reaction solvent usable herein, tetrahydrofuran, 1,2-dimethoxyethane, dichloromethane, chloroform, benzene, toluene and N,N-dimethylformamide may be used. This reaction is carried out at −78° to 100° C. under stirring for 1 to 24 hours, preferably at −30° to 50° C. under stirring for 2 to 15 hours.

Step h: The cinnamate compound of the formula (10) is subjected to the reduction of the double bond thereof and then hydrolysis of ester. Thus it is converted into the carboxylic acid of the formula (11).

The "reduction" as performed herein means hydrogenation and a catalyst such as palladium/carbon or platinum and a solvent such as ethyl acetate, benzene, toluene, methanol, ethanol or dichloromethane are used therefor. This reaction is carried out at 0° to 60° C. under stirring for 1 to 24 hours, preferably at room temperature under stirring for 1 to 10 hours.

The hydrolysis is performed by stirring the compound in an organic solvent such as methanol, ethanol, tetrahydrofuran or dioxane, or a mixture of such an organic solvent with Step i: From a benzyloxy compound of the formula (13), the benzyloxy group is removed by reduction to give a compound of the formula (14).

The "reduction" as performed herein means hydrogenation with the use of, for example, a catalyst such as palladium/carbon or palladium hydroxide/carbon and a solvent such as ethanol, methanol, ethyl acetate or benzene, or Birch reduction with the use of, for example, sodium/liquid ammonia.

Next, the phenol compound of the formula (14) can be converted into the compound of the present invention of formula (I) through the reaction with the compound of the formula (2) similar to that of the step a.

[Route 6]

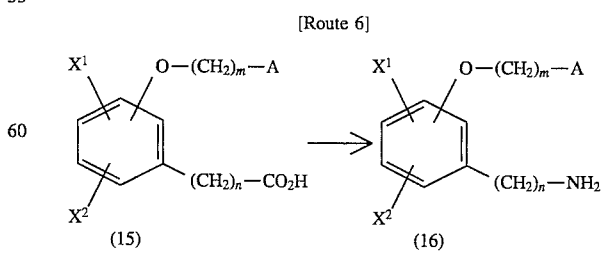

A carboxylic acid of the formula (15) is converted into the compound of the present invention of the formula (16)

through Curtius rearrangement [described in, for example, J.A.C.S., 94, 6203 (1972); J. Praktische Chemie, 50, 275 (1894)] which is commonly employed in the art.

[Route 7]

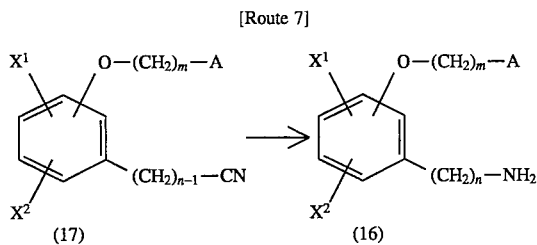

Also, a nitrile of the formula (17) obtained by the methods of the steps f and d is converted into the compound of the formula (16) of the present invention through reduction.

The "reduction" as performed herein means hydrogenation with the use of a catalyst such as palladium/carbon or platinum dioxide and a solvent such as ethanol, ethyl acetate or benzene, or reduction with the use of a reducing agent such as aluminum lithium hydride, sodium bis(methoxyethoxy)aluminum hydride, borane-tetrahydrofuran or sodium trifluoroacetyloxyboron hydride and a solvent such as tetrahydrofuran, ether, 1,2-dimethoxyethane, toluene or benzene. This reaction is carried out at 0° to 150° C. under stirring for 1 to 24 hours, preferably at room temperature to 80° C. under stirring for 2 to 10 hours.

[Route 8]

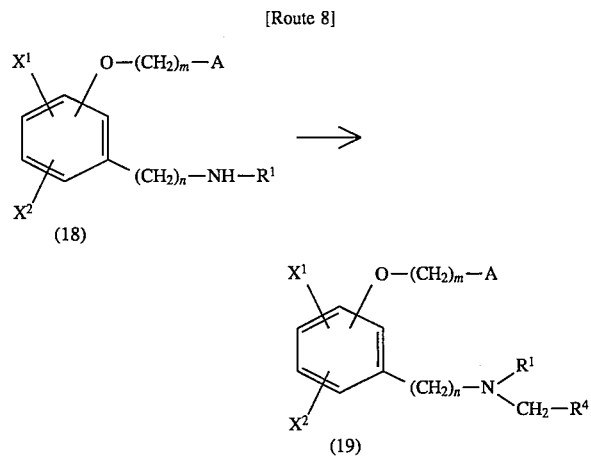

An amine of the formula (18) is reacted with an acid halide represented by a formula $R^4COX$ in the presence of a base and then reduced to give the compound of the formula (19) of the present invention.

As examples of the base usable herein, pyridine, triethylamine and N-methylmorpholine may be used. This reaction is carried out in a solvent such as dichloromethane, chloroform, benzene, toluene, tetrahydrofuran or N,N-dimethylformamide at 0° to 50° C. under stirring for 0.5 to 5 hours.

In the reduction, a reducing agent such as aluminum lithium hydride, sodium bis(methoxyethoxy)aluminum hydride or borane•tetrahydrofuran and a solvent such as tetrahydrofuran, ether, 1,2-dimethoxyethane, toluene or benzene may be used. This reaction is carried out at 0° to 150° C. under stirring for 1 to 24 hours, preferably at room temperature to 80° C. under stirring for 2 to 10 hours.

[Route 9]

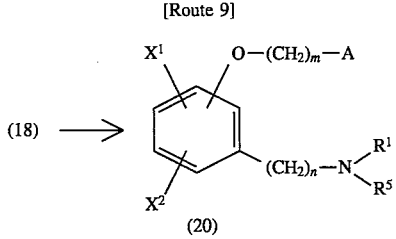

The primary or secondary amine represented by the formula (18) is reacted with a halide represented by the formula $R^5$—X in the presence of a base to give the compound of the present invention represented by the formula (20). When the compound of the formula (18) is a primary amine ($R^1$ is a hydrogen atom), the compound of the present invention represented by the following formula:

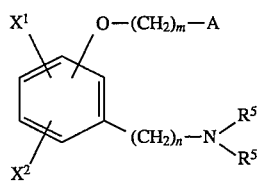

can be obtained by using the base and 2 equivalents or more of the halide represented by the formula $R^5$—X.

Examples of the base to be used herein include organic bases such as pyridine, triethylamine or N-methylmorpholine and inorganic bases such as potassium carbonate, sodium carbonate, potassium hydrogencarbonate, sodium hydrogencarbonate, potassium hydroxide or sodium hydroxide. This reaction is carried out in a solvent such as dichloromethane, benzene, toluene, tetrahydrofuran, N,N-dimethylformamide or ethanol at a temperature of 0° to 100° C. for 2 hours to 4 days, preferably at room temperature for 1 to 2 days, under stirring.

To use the compound of the present invention as a drug, the compound of the present invention is mixed with solid or liquid carriers and formulated into a drug preparation suitable for oral or parenteral administration. Examples of the drug preparation include solid preparations such as tablets, pills, capsules or granules, liquid preparations such as injections, syrups or emulsions and preparations for external use such as ointments or suppositories. These preparations can be produced by the conventional techniques.

The above-mentioned preparations may further contain additives commonly employed in the art, for example, fillers, binders, lubricants, stabilizers, humectants or emulsifiers. For example, an injection may contain a solvent such as distilled water for injection, physiological saline or Ringer solution and a preservative such as methyl parahydroxybenzoate or propyl parahydroxybenzoate. A syrup and an emulsion may contain, for example, sorbitol syrup, methylcellulose, glucose, sucrose syrup, hydroxyethylcellulose, edible oil, glycerol, ethanol or water as well as an emulsifier such as gum arabic or lecithin, or a surfactant such as Tween or Span. A solid preparation may contain a filler such as crystalline cellulose, lactose, corn starch or mannitol, a lubricant such as magnesium stearate or talc, a binder such as hydroxypropylcellulose, hydroxypropylmethylcellulose or poly(vinylpyrrolidone), a disintegrating agent such as calcium carboxymethylcellulose, and a flowability improver such as light anhydrous silicic acid.

The dose of the compound of the present invention for a patient to be treated therewith may vary depending on the age, disease and conditions of the patient. In general, it may be administered to an adult in a dose of from 0.1 to 20 mg/day once to several times.

BEST MODE FOR CARRYING OUT THE INVENTION

To further illustrate the present invention in greater detail, the following Examples and Test Examples will be given.

EXAMPLE 1

Production of
5-bromo-2-(2-phenylethoxy)benzaldehyde 66.02 g of 5-bromosalicylaldehyde was dissolved in 260 ml of N,N-dimethylformamide. Then 113.35 g of anhydrous potassium carbonate and 111.71 ml of (2-bromoethyl)benzene were added thereto and the resulting mixture was stirred at room temperature for 38 hours. After evaporation of the solvent under reduced pressure, ethyl acetate and water were added to the residue and the mixture was separated. The organic layer was collected and dried over anhydrous sodium sulfate. After evaporation of the solvent under reduced pressure, the residue was recrystallized from isopropanol to give 82.62 g of 5-bromo-2-(2-phenylethoxy)benzaldehyde. m.p. 79°–80° C.

By using the corresponding starting materials, the following compounds were obtained by the same method as described above.

3-Fluoro-2-(2-phenylethoxy)benzaldehyde.
  NMR (CDCl$_3$) δ (ppm); 3.13 (2H, t, J=6.8 Hz), 4.50 (2H, dt, J=1.9, 6.8 Hz), 7.06 (1H, m), 7.21–7.37 (6H, m), 7.57 (1H, m), 10.12 (1H, d, J=0.9 Hz).
  MS m/e; 224 (M$^+$).
3-Methoxy-2-(2-phenylethoxy)benzaldehyde.
  NMR (DMSO) δ (ppm); 3.05 (2H, t, J=7.5 Hz), 3.87 (3H, s), 4.38 (2H, dt, J=7.5 Hz), 7.12–7.39 (8H, m), 9.99 (1H, s).
  MS m/e; 256 (M$^+$).
5-Methoxy-2-(2-phenylethoxy)benzaldehyde.
  NMR (CDCl$_3$) δ (ppm); 3.13 (2H, t, J=6.7 Hz), 3.79 (3H, s), 4.26 (2H, dt, J=6.7 Hz), 6.91 (1H, d, J=9.2 Hz), 7.10 (1H, dd, J=3.3, 9.2 Hz), 7.20–7.38 (6H, m), 10.39 (1H, s).
  MS m/e; 256 (M$^+$).
4-Methoxy-2-(2-phenylethoxy)benzaldehyde.
  NMR (CDCl$_3$) δ (ppm); 3.15 (2H, t, J=6.7 Hz), 3.84 (3H, s), 4.26 (2H, t, J=6.7 Hz), 6.41 (1H, d, J=2.2 Hz), 6.53 (1H, dd, J=2.2, 8.7 Hz), 7.21–7.38 (5H, m), 7.80 (1H, d, J=8.7 Hz), 10.28 (1H, s),
  MS m/e; 256 (M$^+$).
2-Methoxy-4-(2-phenylethoxy)benzaldehyde.
  NMR (CDCl$_3$) δ (ppm); 3.12 (2H, t, J=7.0 Hz), 3.88 (3H, s), 4.24 (2H, t, J=7.0 Hz), 6.43 (1H, d, J=2.2 Hz), 6.53 (1H, dd, J=2.2, 8.7 Hz), 7.22–7.39 (5H, m), 7.79 (1H, d, J=8.7 Hz), 10.28 (1H, s).
  MS m/e; 256 (M$^+$).
4-Methoxy-3-(2-phenylethoxy)benzaldehyde.
  NMR (CDCl$_3$) δ (ppm); 3.18 (2H, t, J=7.5 Hz), 3.95 (3H, s), 4.28 (2H, t, J=7.5 Hz), 6.96 (1H, d, J=8.5 Hz), 7.18–7.35 (5H, m), 7.40 (1H, dd, J=1.5 Hz), 7.45 (1H, dd, J=1.5, 8.5 Hz), 9.83 (1H, s).
  MS m/e; 256 (M$^+$).
3-Methoxy-4-(2-phenylethoxy)benzaldehyde.
  NMR (CDCl$_3$) δ (ppm); 3.20 (2H, t, J=7.5 Hz), 3.94 (3H, s), 4.30 (2H, t, J=7.5 Hz), 6.96 (1H, d, J=8.7 Hz), 7.21–7.38 (5H, m), 7.40–7.45 (2H, m), 9.86 (1H, s).
  MS m/e; 256 (M$^+$).
5-Bromo-2-(3-phenylpropoxy)benzaldehyde.
  NMR (DMSO) δ (ppm); 2.10 (2H, m). 2.79 (2H, t, J=7.5 Hz), 4.12 (2H, t, J=7.5 Hz), 7.10–7.35 (6H, m), 7.72–7.83 (2H, m), 10.25 (1H, s).
  MS m/e; 320 (M$^+$+2), 318 (M$^+$).
4-Benzyloxy-3-(2-phenylethoxy)benzaldehyde.
  m.p. 71°–72.5° C. (recrystallized from isopropyl ether).
3-Benzyloxy-4-(2-phenylethoxy)benzaldehyde.
  m.p. 64°–66° C. (recrystallized from isopropyl ether).
5-Chloro-2-(3-phenylpropoxy)benzaldehyde.
  NMR (DMSO) δ (ppm); 2.10 (2H, m), 2.79 (2H, t, J=7.5 Hz), 4.14 (2H, t, J=7.5 Hz), 7.12–7.35 (6H, m), 7.60–7.72 (2H, m),
  10.26 (1H, s).
  MS m/e; 276 (M$^+$+2), 274 (M$^+$).

EXAMPLE 2

Production of
5-chloro-2-(2-phenylethoxy)benzaldehyde 5 g of 5-chlorosalicylaldehyde was dissolved in 300 ml of acetonitrile. After adding 41.48 g of potassium fluoride/alumina (neutral) (2:3) and 17.45 ml of (2-bromoethyl)benzene, the resulting mixture was stirred at room temperature for 63 hours. Then the potassium fluoride/alumina was removed by filtration under sucking and the solvent was evaporated under reduced pressure. The residue was purified by silica gel column chromatography (developing solvent; n-hexane:ethyl acetate=10:1) and recrystallized from isopropyl ether to give 5.58 g of 5-chloro- 2-(2-phenylethoxy)benzaldehyde.
m.p. 73°–74° C.

EXAMPLE 3

Production of 5-fluoro-2-(2-phenylethoxy]benzyl Alcohol

To a solution of 4.99 g of 5-fluorosalicylic acid in 30 ml of methanol, was added 2 ml of conc. sulfuric acid and the mixture was heated under reflux for 18 hours. Then the reaction mixture was ice-cooled and the crystals thus precipitated were collected by filtration and thoroughly washed with cold methanol.

The crystals were dried and then dissolved in 50 ml of N,N-dimethylformamide. After adding 16.54 ml of (2-bromoethyl)benzene and 16.73 g of anhydrous potassium carbonate, the mixture was stirred at room temperature for a day. Then the reaction mixture was concentrated under reduced pressure, poured into water and extracted with ethyl acetate. The organic layer was successively washed with water and a saturated aqueous solution of sodium chloride, dried over anhydrous magnesium sulfate and then filtered. The solvent was evaporated under reduced pressure.

The residue was dissolved in 50 ml of tetrahydrofuran and 1.15 g of aluminum lithium hydride was added thereto in portions under ice-cooling. After stirring for additional 1 hour under ice-cooling, a saturated aqueous solution of sodium sulfate was added dropwise thereto until no hydrogen gas evolved any more. The solid matters thus precipitated were separated by filtration and the residue was subjected to silica gel column chromatography (developing solvent; n-hexane:acetone= 20:1–10:1) to give 7.07 g of 5-fluoro- 2-(2-phenylethoxy)benzyl alcohol.

NMR (CDCl$_3$) δ (ppm); 2.20 (1H, t, J=6.3 Hz, exchangeable with D$_2$O), 3.08 (2H, t, J=6.8 Hz), 4.18 (2H, t, J=6.8 Hz), 4.53 (2H, d, J=6.3 Hz), 6.75 (1H, dd, J=5.0, 10.0 Hz), 6.83–7.00 (2H, m), 7.19–7.38 (5H, m).

MS m/e; 246 (M$^+$).

By using the corresponding starting materials, the following compounds were obtained by the same method as described above.

4-Chloro-2-(2-phenylethoxy)benzyl alcohol.

NMR (CDCl$_3$) δ (ppm); 2.03 (1H, t, J=7.0 Hz, exchangeable with D$_2$O), 3.11 (2H, t, J=7.0 Hz), 4.21 (2H, t, J=7.0 Hz), 4.53 (2H, d, J=7.0 Hz), 6.83 (1H, d, J=1.5 Hz), 6.89 (1H, dd, J=1.5, 9.5 Hz), 7.15 (1H, d, J=9.5 Hz), 7.20–7.40 (5H, m).

MS m/e; 264 (M$^+$+2), 262 (M$^+$).

3,5-Dichloro-2-(2-phenylethoxy)benzyl alcohol.

NMR (CDCl$_3$) δ (ppm); 1.75 (1H, s, exchangeable with D$_2$O), 3.12 (2H, t, J=6.5 Hz), 4.02 (2H, t, J=6.5 Hz), 4.40 (2H, s), 7.22–7.40 (7H, m).

MS m/e; 300 (M$^+$+4), 298 (M$^+$+2), 296 (M$^+$).

3,5-Dibromo-2-(2-phenylethoxy)benzyl alcohol.

NMR (CDCl$_3$) δ (ppm); 1.86 (1H, brs, exchangeable with D$_2$O), 3.13 (2H, t, J=6.8 Hz), 4.17 (2H, t, J=6.8 Hz), 4.41 (2H, s), 7.20–7.38 (5H, m), 7.41 (1H, d, J=3.5 Hz), 7.60 (1H, d, J=3.5 Hz).

MS m/e; 388 (M$^+$+4), 386 (M$^+$+2), 384 (M$^+$).

3-Benzyloxy-4-methoxy-5-(2-phenylethoxy)benzyl alcohol.

NMR (CDCl$_3$) δ (ppm); 1.63 (1H, t, J=6.2 Hz, exchangeable with D$_2$O), 3.13 (2H, t, J=7.0 Hz), 3.76 (3H, s), 4.22 (2H, t, J=7.0 Hz), 4.55 (2H, d, J=6.2 Hz), 5.11 (2H, s), 6.58 (1H, d, J=1.4 Hz), 6.65 (1H, d, J=1.4 Hz), 7.18–7.48 (10H, m).

MS m/e; 364 (M$^+$).

EXAMPLE 4

Production of
5-bromo-2-(2-phenylethoxy)phenylacetic Acid

To a suspension of 0.249 g of aluminum lithium hydride in tetrahydrofuran, was slowly added 20 ml of a solution of 1.67 g of the 5-bromo-2-(2-phenylethoxy)benzaldehyde obtained above in tetrahydrofuran under stirring and ice-cooling. The obtained mixture was further stirred for 2 hours. Then a saturated solution of sodium sulfate was added to the reaction mixture under stirring. After the completion of the gas evolution, the reaction mixture was dried over magnesium sulfate and filtered under sucking, followed by evaporation of the filtrate under reduced pressure.

The residue was dissolved in 10 ml of tetrahydrofuran and 2 ml of hexamethylphosphoric triamide. After adding 0.48 ml of thionyl chloride, the mixture was stirred at room temperature for 20 hours. Then the solvent was evaporated under reduced pressure and the residue was dissolved in ethyl acetate, successively washed with water and a saturated aqueous solution of sodium hydrogencarbonate and dried over anhydrous sodium sulfate, followed by evaporation of the solvent.

The residue was dissolved in 15 ml of acetonitrile and 0.582 g of potassium cyanide and 0.123 g of 18-crown-6-ether were added thereto. The obtained mixture was stirred at room temperature for 18 hours. After adding ethyl acetate, the reaction mixture was successively washed with water and a saturated aqueous solution of sodium hydrogencarbonate, dried over anhydrous sodium sulfate and evaporated under reduced pressure. To the residue, were added 30 ml of ethanol and 10 ml of a 6N aqueous solution of sodium hydroxide and the mixture was heated under reflux for 5 hours. After evaporation of the solvent under reduced pressure, the residue was dissolved in water, washed with ether, acidified with conc. hydrochloric acid and then extracted with ethyl acetate. After drying over anhydrous sodium sulfate, the solvent was evaporated under reduced pressure to give 1.47 g of 5-bromo-2-(2-phenylethoxy)phenylacetic acid.

NMR (DMSO) δ (ppm); 2.99 (2H, t, J=7.5 Hz), 3.47 (2H, s), 4.25 (2H, t, J=7.5 Hz), 6.93 (1H, d, J=10.0 Hz), 7.13–7.41 (7H, m), 12.20 (1H, brs, exchangeable with D$_2$O).

MS m/e; 336 (M$^+$+2), 274 (M$^+$).

The compounds obtained in Examples 1 and 2 were treated in the same manner as that of Example 4 to thereby give the following compounds.

5-Chloro-2-(2-phenylethoxy)phenylacetic acid.

NMR (DMSO) δ (ppm); 2.99 (2H, t, J=7.0 Hz), 3.48 (2H, s), 4.15 (2H, t, J=7.0 Hz), 6.99 (1H, d, J=10.0 Hz), 7.15–7.40 (7H, m), 10.30 (1H, brs, exchangeable with D$_2$O).

MS m/e; 292 (M$^+$+2), 290 (M$^+$).

3-Fluoro-2-(2-phenylethoxy)phenylacetic acid.

m.p. 74°–75° C. (crystallized by acidifying aqueous solution of sodium hydroxide with hydrochloric acid).

3-Methoxy-2-(2-phenylethoxy)phenylacetic acid.

m.p. 88°–89° C. (crystallized by acidifying aqueous solution of sodium hydroxide with hydrochloric acid).

5-Methoxy-2-(2-phenylethoxy)phenylacetic acid.

m.p. 56.5°–57.5° C. (crystallized by acidifying aqueous solution of sodium hydroxide with hydrochloric acid).

4-Methoxy-2-(2-phenylethoxy)phenylacetic acid.

m.p. 107°–108° C. (crystallized by acidifying aqueous solution of sodium hydroxide with hydrochloric acid).

2-Methoxy-4-(2-phenylethoxy)phenylacetic acid.

NMR (CDCl$_3$) δ (ppm); 3.10 (2H, t, J=6.8 Hz), 3.59 (2H, s), 3.79 (3H, s), 4.17 (2H, t, J=6.8 Hz), 6.42–6.47 (2H, m), 7.06 (1H, d, J=9.5 Hz), 7.18–7.37 (5H, m).

MS m/e; 286 (M$^+$).

4-Methoxy-3-(2-phenylethoxy)phenylacetic acid.

m.p. 88°–89° C. (crystallized by acidifying aqueous solution of sodium hydroxide with hydrochloric acid).

3-Methoxy-4-(2-phenylethoxy)phenylacetic acid.

m.p. 97°–100° C. (crystallized by acidifying aqueous solution of sodium hydroxide with hydrochloric acid).

3-Benzyloxy-4-(2-phenylethoxy)phenylacetic acid.

m.p. 116°–119° C. (crystallized by acidifying aqueous solution of sodium hydroxide with hydrochloric acid).

4-Benzyloxy-3-(2-phenylethoxy)phenylacetic acid.

m.p. 110°–112° C. (crystallized by acidifying aqueous solution of sodium hydroxide with hydrochloric acid).

5-Bromo-2-(3-phenylpropoxy)phenylacetic acid.

m.p. 79.5°–81° C. (crystallized by acidifying aqueous solution of sodium hydroxide with hydrochloric acid).

5-Chloro-2-(3-phenylpropoxy)phenylacetic acid.

m.p. 95°–96.5° C. (crystallized by acidifying aqueous solution of sodium hydroxide with hydrochloric acid).

5-Bromo-2-benzyloxyphenylacetic acid.

m.p. 87°–88.5° C. (crystallized by acidifying aqueous solution of sodium hydroxide with hydrochloric acid).

2-Benzyloxy-5-chlorophenylacetic acid.

m.p. 76°–77.5° C. (crystallized by acidifying aqueous solution of sodium hydroxide with hydrochloric acid).

Starting from the benzyl alcohols described in Example 3, the same procedure following the chlorination as described in Example 4 was performed. Thus the following compounds were obtained.

5-Fluoro-2-(2-phenylethoxy)phenylacetic acid.

m.p. 99°–101° C. (crystallized by acidifying aqueous solution of sodium hydroxide with hydrochloric acid).
4-Chloro-2-(2-phenylethoxy)phenylacetic acid.

m.p. 102.5°–104.5° C. (crystallized by acidifying aqueous solution of sodium hydroxide with hydrochloric acid).
3,5-Dichloro-2-(2-phenylethoxy)phenylacetic acid.

m.p. 73°–76° C. (crystallized by acidifying aqueous solution of sodium hydroxide with hydrochloric acid).
3,5-Dibromo-2-(2-phenylethoxy)phenylacetic acid.

m.p. 81°–84° C. (crystallized by acidifying aqueous solution of sodium hydroxide with hydrochloric acid).
3-Benzyloxy-4-methoxy-5-(3-phenylpropoxy)phenylacetic acid.

m.p. 138°–140° C. (recrystallized from toluene).

EXAMPLE 5

Production of
3-[5-bromo-2-(2-phenylethoxy)phenyl]propionic Acid

Under a nitrogen gas stream, 9.1 ml of ethyl diethylphosphonoacetate was dissolved in 60 ml of tetrahydrofuran and then 3.875 g of potassium-t-butoxide dissolved in 30 ml of tetrahydrofuran was added thereto under ice-cooling. The obtained mixture was stirred for 40 minutes. To this reaction mixture, was added 20 ml of a solution of 7 g of 5-bromo-2-(2-phenylethoxy)benzaldehyde in tetrahydrofuran and the obtained mixture was stirred for 18 hours while returning to room temperature. A saturated aqueous solution of sodium hydrogencarbonate was added to the reaction mixture. After evaporation of the solvent under reduced pressure, the residue was dissolved in ethyl acetate and successively washed with a saturated aqueous solution of sodium hydrogencarbonate and water. The organic layer was dried over anhydrous sodium sulfate and the solvent was evaporated under reduced pressure. The product thus obtained was not purified but used in the subsequent reaction as such.

The above-mentioned product was dissolved in 30 ml of ethyl acetate. After adding 0.55 g of platinum dioxide, the mixture was stirred under a hydrogen gas stream at room temperature for 36 hours. The platinum dioxide was filtered through Celite and the filtrate was evaporated under reduced pressure. To the obtained residue, were added 40 ml of a 6N aqueous solution of sodium hydroxide, 50 ml of methanol and 50 ml of dioxane and the resulting mixture was stirred for 3 hours. After evaporation of the solvent under reduced pressure, the residue was dissolved in water, acidified with conc. hydrochloric acid and extracted with ethyl acetate to give 2.88 g of oily 3-[5-bromo-2-(2-phenylethoxy)phenyl] propionic acid.

NMR (DMSO) δ (ppm); 2.35 (2H, t, J=7.5 Hz), 2.70 (2H, t, J=7.5 Hz), 3.03 (2H, t, J=6.3 Hz), 4.18 (2H, t, J=6.3 Hz), 6.88–7.38 (8H, m), 12.09 (1H, brs, exchangeable with $D_2O$).

MS m/e; 350 ($M^+$+2), 348 ($M^+$).

The above procedure was repeated except for replacing the 5-bromo-2-(2-phenylethoxy)benzaldehyde by 3-methoxy-2-(2-phenylethoxy)benzaldehyde or 4-methoxy-3-(2-phenylethoxy)benzaldehyde to give the following compounds.
3-[3-Methoxy-2-(2-phenylethoxy)phenyl]propionic acid.

NMR (DMSO) δ (ppm); 2.35 (2H, t, J=7.5 Hz), 2.67 (2H, t, J=7.5 Hz), 3.00 (2H, t, J=6.3 Hz), 3.75 (3H, s), 4.13 (2H, t, J=6.3 Hz), 6.71–6.98 (3H, m), 7.17–7.25 (5H, m), 12.04 (1H, brs, exchangeable with $D_2O$).

MS m/e; 300 ($M^+$).
3-[4-Methoxy-3-(2-phenylethoxy)phenyl]propionic acid.

m.p. 77.5°–78.5° C. (recrystallized from n-hexane/toluene).

EXAMPLE 6

Production of
N,N-di-n-propyl-2-[4-methoxy-3-(2-phenylethoxy) phenylethylamine Oxalate 0.4 ml of thionyl chloride was added to 0.77 g of 4-methoxy-3-(2-phenylethoxy)phenylacetic acid in 5 ml of toluene and stirred at 90° C. for 4 hours. The reaction mixture was concentrated under reduced pressure and 5 ml of toluene was added thereto again. Then 0.83 g of di-n-propylamine was added dropwise thereto under ice-cooling and stirring and the resulting mixture was further stirred at room temperature overnight. The reaction mixture was washed successively with water, dilute hydrochloric acid, a saturated aqueous solution of sodium hydrogencarbonate and a saturated aqueous solution of sodium chloride, dried over anhydrous magnesium sulfate and filtered followed by evaporation of the solvent under reduced pressure.

A solution of the above residue in 2 ml of tetrahydrofuran was added dropwise to a suspension of 0.21 g of aluminum lithium hydride in 5 ml of tetrahydrofuran at room temperature under stirring. After stirring and heating at reflux for additional 3 hours, the mixture was ice-cooled and a saturated aqueous solution of sodium sulfate was added dropwise thereto until no hydrogen gas evolved any more. The solid matters thus precipitated were filtered and the residue was subjected to silica gel chromatography (developing solvent; n-hexane:ethyl acetate=3:1). From the target fraction, the solvent was evaporated under reduced pressure and the residue was dissolved in ethanol. 0.15 g of oxalic acid was added thereto and dissolved under heating. After evaporation of the solvent under reduced pressure, ether was added for crystallization to give 0.61 g of N,N-di-n-propyl-2-[4-methoxy-3-(2-phenylethoxy)phenyl]ethylamine oxalate.

m.p. 80°–81° C.

By using the corresponding starting materials, the above procedure was repeated and thus the following compounds were obtained. (In the case of a hydrochloride, a 4N solution of hydrogen chloride in ethyl acetate or conc. hydrochloric acid was used in place of the oxalic acid.) N,N-di-n-propyl-2-[4-methoxy-3-(2-phenylethoxy)phenyl]ethylamine hydrochloride.

m.p. 99°–100° C. (recrystallized from ethyl acetate).
N-2-[3-Methoxy-2-(2-phenylethoxy)phenyl]ethylpyrrolidine oxalate.

m.p. 126°–128° C. (recrystallized from ethyl acetate).
N-2-[3-Methoxy-2-(2-phenylethoxy)phenyl]ethylmorpholine oxalate.

m.p. 163°–165° C. (recrystallized from ethanol).
N-2-[3-Methoxy-2-(2-phenylethoxy)phenyl]ethyl-N'-phenylpiperazine oxalate.

m.p. 198°–200° C. (recrystallized from ethanol).
N-2-[3-Methoxy-2-(2-phenylethoxy)phenyl]ethyl-N'-(2-pyridyl)piperazine oxalate.

m.p. 171°–173° C. (recrystallized from ethanol).
N-2-[4-Methoxy-3-(2-phenylethoxy)phenyl]ethylpyrrolidine oxalate.

m.p. 140°–142° C. (recrystallized from isopropanol).

N-2-[4-Methoxy-3-(2-phenylethoxy)phenyl]ethylmorpholine oxalate.
  m.p. 158°–160° C. (recrystallized from ethanol).
N-2-[4-Methoxy-3-(2-phenylethoxy)phenyl]ethyl-N'-phenylpiperazine oxalate.
  m.p. 182°–185° C. (recrystallized from ethanol).
N-2-[4-Methoxy-3-(2-phenylethoxy)phenyl]ethyl-N'-(2-pyridyl)piperazine oxalate.
  m.p. 168°–170° C. (recrystallized from ethanol).
N-2-[5-Chloro-2-(2-phenylethoxy)phenyl]ethyl-N'-(2-methoxyphenyl)piperazine dihydrochloride.
  m.p. 136°–138° C. (recrystallized from isopropanol).
N,N-Di-n-propyl-2-[5-methoxy-2-(2-phenylethoxy)phenyl]ethylamine hydrochloride.
  m.p. 92°–93° C. (recrystallized from ethyl acetate).
N,N-Di-n-propyl-2-[3-methoxy-4-(2-phenylethoxy)phenyl]ethylamine oxalate.
  m.p. 108°–110° C. (recrystallized from isopropanol).
N,N-Di-n-propyl-2-[2-methoxy-4-(2-phenylethoxy)phenyl]ethylamine oxalate.
  m.p. 132°–133° C. (recrystallized from ethyl acetate).
N-2-[4-Methoxy-3-(2-phenylethoxy)phenyl]ethyl-N'-(2-methoxyphenyl)piperazine dihydrochloride.
  m.p. 172°–173° C. (recrystallized from methanol).
N,N-Di-n-propyl-2-[4-methoxy-2-(2-phenylethoxy)phenyl]ethylamine oxalate.
  m.p. 137°–138° C. (recrystallized from isopropanol).
N-2-[5-Chloro-2-(2-phenylethoxy)phenyl]ethylpyrrolidine oxalate.
  m.p. 171°–173° C. (recrystallized from ethanol).
N-2-[5-Chloro-2-(2-phenylethoxy)phenyl]ethylmorpholine oxalate.
  m.p. 181°–183° C. (recrystallized from ethanol).
N,N-Di-n-propyl-2-[3-methoxy-2-(2-phenylethoxy)phenyl]ethylamine oxalate.
  m.p. 135°–137° C. (recrystallized from ethanol).
N,N-Di-n-propyl-2-[3-methoxy-2-(2-phenylethoxy)phenyl]ethylamine hydrochloride.
  m.p. 105°–107° C. (recrystallized from ethyl acetate/isopropyl ether).
N,N-Di-n-propyl-2-[2-(2-phenylethoxy)phenyl]ethylamine oxalate.
  m.p. 139°–141° C. (recrystallized from ethyl acetate/isopropyl ether).
N,N-Di-n-propyl-2-[4-benzyloxy-3-(2-phenylethoxy)phenyl]ethylamine hydrochloride.
  m.p. 96°–98° C. (recrystallized from ethyl acetate).
N,N-Di-n-propyl-2-[3-benzyloxy-4-(2-phenylethoxy)phenyl]ethylamine oxalate.
  m.p. 110°–111° C. (recrystallized from ethyl acetate).
N,N-Di-n-propyl-2-[3-benzyloxy-4-methoxy-5-(2-phenylethoxy)phenyl] ethylamine hydrochloride.
  NMR (CDCl$_3$) δ (ppm); 0.98 (6H, t, J=7.3 Hz), 1.70–1.98 (4H, m), 2.85–3.01 (4H, m), 3.07 (4H, brs), 3.13 (2H, t, J=6.9 Hz), 3.75 (3H, s), 4.20 (2H, t, J=6.9 Hz), 5.11 (2H, s), 6.15 (1H, d, J=1.9 Hz), 6.46 (1H, d, J=1.9 Hz), 7.13–7.48 (10H, m), 12.28 (1H, brs, exchangeable with D$_2$O).
  MS m/e; 462 (M$^+$+1).
N,N-Di-n-propyl-3-[4-methoxy-3-(2-phenylethoxy)phenyl]propylamine oxalate.
  m.p. 104+–105° C. (recrystallized from ethyl acetate).
N,N-Di-n-propyl-3-[4-methoxy-3-(2-phenylethoxy)phenyl]propylamine hydrochloride.
  m.p. 83°–84° C. (recrystallized from ethyl acetate).
N,N-Di-n-propyl-3-[3-methoxy-2-(2-phenylethoxy)phenyl]propylamine oxalate.
  m.p. 114°–115° C. (recrystallized from ethyl acetate).

N,N-Di-n-propyl-2-[3-benzyloxy-4-methoxyphenyl]ethylamine oxalate.
  m.p. 126°–127° C. (recrystallized from ethanol).
N,N-Di-n-propyl-2-[2-benzyloxy-3-methoxyphenyl]ethylamine oxalate.
  m.p. 124°–126° C. (recrystallized from ethanol).

EXAMPLE 7

Production of N,N-di-n-propyl-2-[5-bromo-2-(2-phenylethoxy)phenyl] ethylamine Oxalate To 0.184 g of aluminum lithium hydride, was added 10 ml of tetrahydrofuran. Then 15 ml of a tetrahydrofuran solution containing 1.47 g of 5-bromo-2-(2-phenylethoxy)phenylacetic acid was added thereto under ice-cooling and stirred for 2 hours. Next, a saturated aqueous solution of sodium sulfate was added to the reaction mixture under stirring. After the completion of the gas evolution, the reaction mixture was dried over magnesium sulfate and filtered under sucking. After evaporation of the filtrate under reduced pressure, the residue was dissolved in 10 ml of tetrahydrofuran and 2 ml of hexamethylphosphoric triamide. Then 0.48 ml of thionyl chloride was added thereto and the resulting mixture was stirred at room temperature for 2 hours. After evaporation of the solvent under reduced pressure, the residue was dissolved in ethyl acetate, successively washed with water and a saturated aqueous solution of sodium hydrogencarbonate and dried over anhydrous sodium sulfate, followed by evaporation of the solvent under reduced pressure. To the residue, was added 11.3 ml of di-n-propylamine and the mixture was heated at reflux for 26 hours. After evaporation of the solvent under reduced pressure, the residue was dissolved in ethyl acetate, successively washed with a 1N aqueous solution of sodium hydroxide and water and dried over anhydrous sodium sulfate, followed by evaporation of the solvent under reduced pressure. The residue was purified by silica gel column chromatography (developing solvent; n-hexane:ethyl acetate =5:1) and 0.045 g of oxalic acid was added to the oily product thus obtained. After recrystallizing from isopropanol, 200 mg of N,N-di-propyl-2-[5-bromo-2-(2phenylethoxy)phenyl] ethylamine oxalate was obtained.
  m.p. 160°–161° C.

By using the corresponding starting materials, the above procedure was repeated to thereby give the following compounds.
N-2-[5-Chloro-2-(2-phenylethoxy)phenyl]ethyl-N'-(2-pyridyl)piperazine oxalate.
  m.p. 165°–167° C. (recrystallized from ethanol).
N-2-[5-Chloro-2-(2-phenylethoxy)phenyl]ethyl-N'-(2pyrimidyl)piperazine oxalate.
  m.p. 176°–178° C. (recrystallized from ethanol).
N,N-Di-propyl-2-(2-benzyloxy-5-chlorophenyl)ethylamine oxalate.
  m.p. 161.5°–163° C. (recrystallized from ethanol).

EXAMPLE 8

Production of N,N-di-n-propyl,3-[5-bromo-2(2-phenylethoxy)phenyl] propylamine Oxalate 1.216 g of 3-[5-bromo-2-(2-phenylethoxy)phenyl]propionic acid was dissolved in 20 ml of benzene and 1.2 ml of thionyl chloride was added thereto. Then the resulting mixture was heated at reflux for 20 minutes. After evaporation of the solvent under reduced pressure, the residue was dissolved in 10 ml of benzene. 3 ml of di-n-propylamine was added thereto and the mixture was stirred for 2 hours. After evaporation of the solvent under reduced pressure, the residue was successively washed with 1N hydrochloric acid, a 1N aqueous solution of sodium hydroxide and water, and dried over anhydrous sodium sulfate, followed by evaporation of the solvent under reduced pressure.

The residue obtained above was dissolved in 20 ml of tetrahydrofuran. Then 9.2 ml of a 1M solution of borane•tetrahydrofuran complex salt in tetrahydrofuran was added thereto and the mixture was heated under reflux for 3 hours. After cooling, 10 ml of methanol was added and the solvent was evaporated under reduced pressure. 40 ml of conc. hydrochloric acid was added to the residue and the resulting mixture was heated at reflux for 1 hour. The reaction mixture was neutralized with a 6N aqueous solution of sodium hydroxide, extracted with ethyl acetate and dried over anhydrous sodium sulfate, followed by evaporation of the solvent under reduced pressure. The residue was purified by silica gel column chromatography (developing solvent; n-hexane: ethyl acetate=10:1) and 118 mg of oxalic acid was added thereto. After recrystallizing from ethyl acetate, 516 mg of N,N-di-propyl-3-[5-bromo-2-(2-phenylethoxy)phenyl]propylamine oxalate was obtained.

m.p. 104°–105° C.

By replacing the 3-[5-bromo-2-(2-phenylethoxy)phenyl]propionic acid by the corresponding starting materials, the above procedure was repeated and thus the following compounds were obtained. (In the case of a hydrochloride, a 4N solution of hydrogen chloride in ethyl acetate or conc. hydrochloric acid was used in place of the oxalic acid.)

N,N-Di-n-propyl-2-[3,5-dichloro-2-(2-phenylethoxy)phenyl]ethylamine oxalate.

m.p. 152°–153° C. (recrystallized from ethanol).

N,N-Di-n-propyl-2-[5-fluoro-2-(2-phenylethoxy)phenyl]ethylamine hydrochloride.

m.p. 85°–86° C. (recrystallized from toluene).

N,N-Di-n-propyl-2-[3,5-dibromo-2-(2-phenylethoxy)phenyl]ethylamine oxalate.

m.p. 152°–153° C. (recrystallized from isopropanol).

N,N-Di-n-propyl-2-[4-chloro-2-(2-phenylethoxy)phenyl]ethylamine hydrochloride.

m.p. 93°–94° C. (recrystallized from ethyl acetate).

N,N-Di-n-propyl-2-[3-fluoro-2-(2-phenylethoxy)phenyl]ethylamine oxalate.

m.p. 137°–138° C. (recrystallized from ethanol).

N,N-Di-n-propyl-2-[5-chloro-2-(3-phenylpropoxy)phenyl]ethylamine oxalate.

m.p. 140.5°–141.5° C. (recrystallized from isopropanol).

N,N-Di-n-propyl-2-[5-bromo-2-(3-phenylpropoxy)phenyl]ethylamine oxalate.

m.p. 138°–139° C. (recrystallized from isopropanol).

N,N-Dimethyl-2-[5-chloro-2-(2-phenylethoxy)phenyl]ethylamine hydrochloride.

m.p. 130°–131° C. (recrystallized from ethyl acetate).

N-2-[5-Chloro-2-(2-phenylethoxy)phenyl]ethylpiperidine hydrochloride.

m.p. 154.5°–155.5° C. (recrystallized from ethyl acetate).

N-2-[5-Chloro-2-(2-phenylethoxy)phenyl]ethylhomopiperidine hydrochloride.

m.p. 142°–143° C. (recrystallized from ethyl acetate).

EXAMPLE 9

Production of
N,N-di-n-propyl-3-[5-chloro-2-(2-phenylethoxy)phenyl] propylamine Oxalate (1) Production of 3-[5-chloro-2-(2-phenylethoxy)phenyl] propanol In an argon gas stream, 3.49 g of potassium t-butoxide was added to a solution of 8.36 g of ethyl diethylphosphonoacetate in 100 ml of tetrahydrofuran under ice-cooling. The obtained mixture was then stirred at the same temperature for 1 hour. Next, a solution of 5.40 g of 5-chloro-2-(2-phenylethoxy)benzaldehyde in 30 ml of tetrahydrofuran was added dropwise to the reaction mixture and the resulting mixture was stirred at the same temperature for 1 hour and then at room temperature for 19 hours. After adding 30 ml of a saturated aqueous solution of sodium hydrogencarbonate, the mixture was extracted with ethyl acetate and dried over anhydrous magnesium sulfate. After evaporation of the solvent under reduced pressure, 11.56 g of crude ethyl 5-chloro-2-(2-phenylethoxy)cinnamate was obtained. This compound was not purified any more but used in the subsequent reaction as such.

570 mg of platinum dioxide was suspended in a solution of 11.39 g of the crude ethyl 5-chloro-2-(2-phenylethoxy)cinnamate in 80 ml of ethyl acetate and stirred in a hydrogen gas stream at room temperature for 4.5 hours. Filtering through Celite and evaporating under reduced pressure gave 10.76 g of crude ethyl 3-[5-chloro-2-(2-phenylethoxy)phenyl] propionate. This compound was not purified any more but used in the subsequent reaction as such.

1.84 g of aluminum lithium hydride was added to a solution of 10.76 g of the crude ethyl 3-[5-chloro-2-(2-phenylethoxy)phenyl] propionate in 100 ml of tetrahydrofuran under ice-cooling and the mixture was stirred at the same temperature for 1 hour. Then 25% aqueous ammonia was added thereto until no hydrogen gas evolved any more. After filtering with the use of Celite and anhydrous magnesium sulfate, the solvent was evaporated under reduced pressure. The residue thus obtained was subjected to silica gel column chromatography (developing solvent; ethyl acetate:n-hexane =1:9) to give 3.31 g of 3-[5-chloro-2-(2-phenylethoxy)phenyl] propanol.

NMR (CDCl$_3$) δ (ppm); 1.59–1.82 (2H, m), 1.67 (1H, brs, exchangeable with D$_2$O), 2.60 (2H, t, J=7.5 Hz), 3.09 (2H, t, J=6.5 Hz), 3.55 (2H, t, J=6.0 Hz), 4.17 (2H, t, J=6.5 Hz), 6.74 (1H, d, J=10.0 Hz), 7.02–7.15 (2H, m), 7.20–7.40 (5H, m).

MS m/e; 292 (M$^+$+2), 290 (M$^+$).

(2) Production of N,N-di-n-propyl-3-[5-chloro-2-(2-phenylethoxy)phenyl] propylamine oxalate 1.22 ml of thionyl chloride was added to a solution of 3.24 g of 3-[5-chloro-2-(2-phenylethoxy)phenyl]propanol and 5 ml of hexamethylphosphoric triamide in 25 ml of tetrahydrofuran under ice-cooling and stirred at room temperature for 2 hours. The reaction mixture was poured into water (100 ml), extracted with ethyl acetate, successively washed with water twice and a saturated aqueous solution of sodium hydrogencarbonate 4 times and dried over anhydrous magnesium sulfate. After evaporation of the solvent under reduced pressure, 3.21 g of crude 4-chloro-2-( 3-chloropropyl)-1-(2-phenylethoxy)benzene was obtained. This compound was not purified any more but used in the subsequent reaction.

To 604 mg of the crude 4-chloro-2-(3-chloropropyl)-1-( 2-phenylethoxy)benzene, was added 5 ml of di-n-propylamine and the resulting mixture was stirred at 120° C. for 39 hours. After diluting with methylene chloride, the mixture was successively washed with a saturated aqueous solution of sodium hydrogencarbonate and a saturated aqueous solution of sodium chloride and dried over anhydrous magnesium sulfate. After evaporation of the solvent under reduced pressure, the obtained residue was subjected to silica gel column chromatography (developing solvent; ethyl acetate:n-hexane =1:5) to give 0.50 g of N,N-di-n-propyl-3-[5-chloro-2-(2-phenylethoxy)phenyl] propylamine.

To a solution of 0.50 g of N,N-di-n-propyl-3-[5-chloro-2-(2-phenylethoxy)phenyl]propylamine in 10 ml of ethanol, was added a solution of 120 mg of oxalic acid in 5 ml of ethanol. After evaporation of the solvent, the obtained crystals were recrystallized from ethyl acetate to give 380 mg of N,N-di-n-propyl-3-[5-chloro-2-(2-phenylethoxy)phenyl] propylamine oxalate.

m.p. 100°–102° C.

By replacing the 5-chloro-2-(2-phenylethoxy)benzaldehyde by the corresponding starting materials, the substantially same procedure as described above was performed to give the following compounds. (In the case of a hydrochloride, a 4N solution of hydrogen chloride in ethyl acetate or conc. hydrochloric acid was used in place of the oxalic acid.)

N-3-[5-Chloro-2-(2-phenylethoxy)phenyl]propyl-N'-(2-pyridyl)piperazine oxalate.

m.p. 150°–152° C. (recrystallized from ethanol).

N-3-[5-Chloro-2-(2-phenylethoxy)phenyl]propyl-N'-(2-pyrimidyl)piperazine oxalate.

m.p. 151°–153° C. (recrystallized from ethanol).

N-3-[5-Chloro-2-(2-phenylethoxy)phenyl]propyl-N'-[2-(6-methylpyridyl)piperazine oxalate.

m.p. 160°–162° C. (recrystallized from isopropanol).

N-3-[5-Chloro-2-(2-phenylethoxy)phenyl]propyl-N'-phenylpiperazine oxalate.

m.p. 163°–165° C. (recrystallized from ethanol).

N-3-[5-Chloro-2-(2-phenylethoxy)phenyl]propyl-N'-(2-methoxyphenyl)piperazine oxalate.

m.p. 141°–143° C. (recrystallized from ethyl acetate/n-hexane).

N-3-[5-Chloro-2-(2-phenylethoxy)phenyl]propylpyrrolidine hydrochloride.

NMR (CDCl$_3$) δ ppm; 1.84–2.30 (6H, m), 2.42–2.68 (4H, m), 2.70–2.88 (2H, m), 3.12 (2H, t, J=6.5 Hz), 3.57–3.75 (2H, m), 4.19 (2H, t, J=6.5 Hz), 6.76 (1H, d, J=8.7 Hz), 7.05 (1H, d, J=2.6 Hz), 7.13 (1H, dd, J=2.6, 8.7 Hz), 7.17–7.39 (5H, m), 12.24 (1H, brs, exchangeable with D$_2$O).

MS m/e; 360 (M$^+$+3), 358 (M$^+$+1).

The same procedure as that of Example 9 (1) was repeated except for replacing 5-chloro-2-(2-phenylethoxy)benzaldehyde by 5-chloro-2-(3-phenylpropoxy)benzaldehyde to thereby give the following compound.

3-[5-Chloro-2-(3-phenylpropoxy)phenyl]propanol.

NMR (CDCl$_3$) δ ppm; 1.62 (1H, t, J=5.8 Hz, exchangeable with D$_2$O), 1.79–1.93 (2H, m), 2.15–2.19 (2H, m), 2.72 (2H, t, J=7.4 Hz), 2.81 (2H, t, J=7.6 Hz), 3.63 (2H, m), 3.95 (2H, t, J=6.3 Hz), 6.71 (1H, d, J=8.8 Hz), 7.07–7.34 (7H, m).

MS m/e; 306 (M$^+$+2), 304 (M$^+$).

Next, the following compound was obtained by the same method as that of Example 9 (2).

N-3-[5-Chloro-2-(3-phenylpropoxy)phenyl]propylpyrrolidine hydrochloride.

m.p. 113.5°–115.5° C. (recrystallized from ethyl acetate).

EXAMPLE 10

Production of
N,N-di-n-propyl-4-[5-chloro-2-(2-phenylethoxy)phenyl] butylamine Oxalate (1) Production of 4-[5-chloro-2-(2-phenylethoxy)phenyl] butanol To a solution of 1.62 g of crude 4-chloro-2-(3-chloropropyl)- 1-(2-phenylethoxy)benzene in 20 ml of acetonitrile, were added 681 mg of potassium cyanide and 138 mg of 18-crown-6 and heated under reflux for 11 hours. After cooling, the solvent was evaporated under reduced pressure and ethyl acetate and water were added to the residue thus obtained. Then the ethyl acetate layer was collected, washed thrice with water and a saturated aqueous solution of sodium hydrogencarbonate and dried over anhydrous magnesium sulfate. After evaporation of the solvent under reduced pressure, 1.55 g of crude 4-[5-chloro-2-(2-phenylethoxy)phenyl]butyronitrile was obtained. This compound was not purified any more but used in the subsequent reaction.

15 ml of a 20% (w/v) aqueous solution of potassium hydroxide was added to a solution of 1.53 g of the crude 4-[5-chloro-2-(2-phenylethoxy)phenyl]butyronitrile in 15 ml of ethanol and the resulting mixture was heated under reflux for 17 hours. After evaporation of the ethanol under reduced pressure, conc. hydrochloric acid was added dropwise to the reaction mixture until it became acidic. Then the reaction mixture was extracted with ethyl acetate and dried over anhydrous magnesium sulfate. After evaporation of the solvent under reduced pressure, 1.41 g of crude 4-[5-chloro-2-(2-phenylethoxy)phenyl]butyric acid was obtained. This compound was not purified any more but used in the subsequent reaction.

246 mg of aluminum lithium hydride was added under ice-cooling to a solution of 1.38 g of the crude 4-[5-chloro-2-(2-phenylethoxy)phenyl]butyric acid in 20 ml of tetrahydrofuran and the resulting mixture was stirred at the same temperature for 30 minutes. Next, 25% aqueous ammonia was added thereto until no hydrogen evolved any more. After filtering with the use of Celite and anhydrous magnesium sulfate, the solvent was evaporated under reduced pressure. The obtained residue was subjected to silica gel column chromatography (developing solvent; ethyl acetate:n-hexane =1:8) to give 0.86 g of 4-[5-chloro-2-(2-phenylethoxy)phenyl] butanol.

NMR (CDCl$_3$) δ (ppm); 1.40 (1H, s, exchangeable with D$_2$O), 1.47–1.68 (4H, m), 2.54 (2H, m), 3.10 (2H, t, J=6.5 Hz), 3.59 (2H, m), 4.15 (2H, t, J=6.5 Hz), 6.71 (1H, d, J=10.0 Hz), 7.01–7.15 (2H, m), 7.18–7.40 (5H, m).

MS m/e; 306 (M$^+$+2), 304 (M$^+$).

(2) Production of N,N-di-n-propyl-4-[5-chloro-2-(2-phenylethoxy)phenyl] butylamine Oxalate 0.31 ml of thionyl chloride was added under ice-cooling to a solution of 0.86 g of 4-[5-chloro-2-(2-phenylethoxy)phenyl] butanol and 4 ml of hexamethylphosphoric triamide in 20 ml of tetrahydrofuran and the resulting mixture was stirred at room temperature for 2 hours. The reaction mixture was poured into water (100 ml), extracted with ethyl acetate, successively washed with water twice and a saturated aqueous solution of sodium hydrogencarbonate 4 times and dried over anhydrous magnesium sulfate. After evaporation of the solvent under reduced pressure, 0.91 g of crude 4-chloro-2-(4-chlorobutyl)-1-(2-phenylethoxy)benzene was obtained. This compound was not purified any more but used in the subsequent reaction.

To 0.91 g of the crude 4-chloro-2-(4-chlorobutyl)-1-(2-phenylethoxy)benzene, was added 10 ml of di-n-propylamine and the resulting mixture was stirred at 120° C. for 38 hours. After diluting with methylene chloride, the mixture was successively washed with a saturated aqueous solution of sodium hydrogencarbonate and a saturated aqueous solution of sodium chloride and dried over anhydrous magnesium sulfate. After evaporation of the solvent under reduced pressure, the obtained residue was subjected to silica gel column chromatography (developing solvent; ethyl acetate:n-hexane =1:6) to give 1.07 g of N,N-di-n-propyl-4-[5-chloro-2-(2-phenylethoxy)phenyl] butylamine. To a solution of 1.07 g of N,N-di-n-propyl-4-[5-chloro-2-(2-phenylethoxy)phenyl]butylamine in 10 ml of ethanol, was added a solution of 123 mg of oxalic acid in 5 ml of ethanol. After evaporation of the solvent under reduced pressure, the obtained crystals were recrystallized from ethyl acetate to give 421 mg of N,N-di-n-propyl- 4-[5-chloro-2-(2-phenylethoxy)phenyl]butylamine oxalate.

m.p. 80°–82° C.

EXAMPLE 11

Production of
N,N-di-n-propyl-2-[5-chloro-2-(2-phenylethoxy) phenyl]ethylamine Oxalate 2.00 g of N,N-di-n-propyl-2-(2-benzyloxy-5-chlorophenyl)ethylamine oxalate was suspended in ethyl acetate and thoroughly shaken with a 10% solution of potassium hydroxide. Then the organic layer was collected, successively washed with water and a saturated aqueous solution of sodium chloride, dried over anhydrous magnesium sulfate and filtered, followed by evaporation of the solvent under reduced pressure.

The residue obtained above was dissolved in 20 ml of ethanol and 0.48 ml of conc. hydrochloric acid and 200 mg of 5% palladium/carbon were added thereto. Then hydrogenation was performed under stirring for 10 hours. Then the catalyst was filtered off and the solvent was evaporated under reduced pressure. The obtained residue was dissolved in 20 ml of N,N-dimethylformamide, and 3.00 g of 2-bromoethylbenzene and 2 g of potassium carbonate were added thereto. After stirring at room temperature for a day, the reaction mixture was concentrated under reduced pressure. After adding water, the mixture was extracted with ethyl acetate. The organic layer was successively washed with water and a saturated aqueous solution of sodium chloride, dried over anhydrous magnesium sulfate and filtered. After evaporation of the solvent under reduced pressure, the residue was subjected to silica gel chromatography (developing solvent; dichloromethane:acetone=20:1–5:1). The target fraction was concentrated and dissolved in ethanol. Then 100 mg of oxalic acid was added thereto and the solvent was evaporated under reduced pressure to give a solid matter. This solid matter was recrystallized from ethanol to give 0.24 g of N,N-di-n-propyl-2-[5-chloro-2-(2-phenylethoxy)phenyl] ethylamine oxalate.

m.p. 166°–167° C.

By using the corresponding starting materials, the substantially same procedure as described above was performed to give the following compounds. (In the case of a hydrochloride, a 4N solution of hydrogen chloride in ethyl acetate or conc. hydrochloric acid was used in place of the oxalic acid.)

N,N-Di-n-propyl-2-[4-methoxy-3-[2-(4-fluorophenyl)ethoxy]phenyl] ethylamine hydrochloride.
 m.p. 114°–116° C. (recrystallized from ethyl acetate).
N,N-Di-n-propyl-2-[4-methoxy-3-[2-(3-chlorophenyl)ethoxy]phenyl] ethylamine hydrochloride.
 m.p. 79°–80° C. (recrystallized from isopropyl ether).
N,N-Di-n-propyl-2-[4-methoxy-3-[2-(4-methoxyphenyl)ethoxy]phenyl] ethylamine oxalate.
 m.p. 110°–111° C. (recrystallized from ethyl acetate).
N,N-Di-n-propyl-2-[3-[2-(4-benzyloxyphenyl)ethoxy]-4methoxyphenyl] ethylamine.
 NMR (CDCl$_3$) δ (ppm); 0.86 (6H, t, J=7.1 Hz), 1.35–1.58 (4H, m), 2.35–2.50 (4H, m), 2.64 (4H, s), 3.10 (2H, t, J=7.5 Hz), 3,83 (3H, s), 4.16 (2H, t, J=7.5 Hz) , 5.05 (2H, s), 6.68–6.75 (2H, m), 6.79 (1H, d, J=9.0 Hz), 6.93 (2H, d, J=8.5 Hz), 7.21 (2H, d, J=8.5 Hz), 7.27–7.48 (5H, m).
 MS m/e; 462 (M$^+$+1).
N,N-Di-n-propyl-2-[4-methoxy-3-[2-(3,4-dimethoxyphenyl)ethoxy] phenyl]ethylamine oxalate.
 m.p. 132°–134° C. (recrystallized from isopropyl alcohol).
N,N-Di-n-propyl-2-[4-methoxy-3-[2-(2-thienyl)ethoxy] phenyl] ethylamine hydrochloride.
 m.p. 96°–98° C. (recrystallized from ethyl acetate).
N,N-Di-n-propyl-2-[3-methoxy-2-(3-phenylpropoxy)phenyl]ethylamine oxalate.
 m.p. 113°–114° C. (recrystallized from ethyl acetate).
N,N-Di-n-propyl-2-[4-methoxy-3-(3-phenylpropoxy)phenyl]ethylamine oxalate.
 m.p. 82°–83° C. (recrystallized from isopropanol).

EXAMPLE 12

Production of
2-[4-methoxy-3-(2-phenylethoxy)phenyl]ethylamine Hydrochloride 1.50 g of 2-[4-methoxy-3-(2-phenylethoxy)phenyl]propionic acid, 1.65 g of diphenylphosphoryl azide and 0.61 g of triethylamine were heated under reflux in t-butanol for 3 hours. After evaporation of the solvent under reduced pressure, the residue was dissolved in ethyl acetate, successively washed with water, a saturated aqueous solution of sodium hydrogencarbonate and a saturated aqueous solution of sodium chloride, dried over anhydrous sodium sulfate and filtered, followed by evaporation of the solvent under reduced pressure.

To the residue thus obtained, was added 20 ml of a 4M solution of hydrogen chloride in ethyl acetate and the mixture was stirred at room temperature for 30 minutes. After evaporation of the solvent under reduced pressure, the remaining crystals were recrystallized from isopropanol to give 650 mg of 2-[4-methoxy-3-(2-phenylethoxy)phenyl] ethylamine hydrochloride.

m.p. 114°–115° C.

EXAMPLE 13

Production of
2-[4-methoxy-3-(2-phenylethoxy)phenyl]ethylamine Hydrochloride 2.04 ml of trifluoroacetic acid was added dropwise to a suspension of 3.60 g of crude 4-methoxy-3-(2-phenylethoxy)phenylacetonitrile obtained in the same manner as that of Example 4 and 1.00 g of sodium boron hydride in 15 ml of tetrahydrofuran under stirring. Then the resulting mixture was heated under reflux for 1 hour. After cooling the reaction mixture to room temperature, 1.00 ml of water and 4.00 ml of conc. hydrochloric acid were successively added dropwise thereto and the mixture was heated under reflux for 1 hour again. After cooling to room temperature, the reaction mixture was made alkaline with a 10N aqueous solution of sodium hydroxide, extracted with dichloromethane, dried over anhydrous sodium sulfate and filtered. Then 1.65 ml of conc. hydrochloric acid was added to the filtrate and the solvent was evaporated under reduced pressure. The remaining crystals were recrystallized from isopropanol to give 2.61 g of 2-[4-methoxy-3-(2-phenylethoxy)phenyl]ethylamine hydrochloride.

m.p. 114°–115° C.

EXAMPLE 14

Production of
N-n-propyl-2-[4-methoxy-3-(2-phenylethoxy)phenyl] ethylamine Hydrochloride 165 mg of propionyl chloride was added under ice-cooling to a solution of 500 mg of 2-[4-methoxy-3-(2-phenylethoxy)phenyl] ethylamine hydrochloride and 385 mg of pyridine in 10 ml of dichloromethane and the mixture was stirred at room temperature for 2 hours. The reaction mixture was then poured into water and extracted with ethyl acetate. The organic layer was successively washed with water, dilute hydrochloric acid, a saturated aqueous solution of sodium hydrogencarbonate and a saturated aqueous solution of sodium chloride, dried over anhydrous sodium sulfate and filtered, followed by evaporation of the solvent under reduced pressure.

To the residue thus obtained, were added 10 ml of tetrahydrofuran and 185 mg of aluminum lithium hydride and the mixture was stirred while heating under reflux for 3 hours. The reaction mixture was ice-cooled and then a saturated aqueous solution of sodium sulfate was added dropwise thereto until no hydrogen gas evolved any more. The solid matters thus precipitated were filtered off. After evaporation of the solvent under reduced pressure, the filtrate was dissolved in ethyl acetate and a 4N solution of hydrogen chloride in ethyl acetate was added thereto. After evaporation of the solvent under reduced pressure, the residue was recrystallized from isopropanol to give 101 mg of N-n-propyl-2-[4-methoxy-3-(2-phenylethoxy)phenyl] ethylamine hydrochloride.

m.p. 134°–136° C.

EXAMPLE 15

Production of
N,N-di-n-propyl-2-[4-hydroxy-3-(2-phenylethoxy) phenyl] ethylamine Hydrochloride 6.50 g of N,N-di-n-propyl-2-[4-benzyloxy-3-(2phenylethoxy)phenyl] ethylamine hydrochloride was added to a mixture of 65 ml of ethyl acetate and 21 ml of a 1N aqueous solution of sodium hydroxide. After stirring for 20 minutes, the organic layer was collected, washed with a saturated aqueous solution of sodium chloride, dried over anhydrous sodium sulfate and filtered, followed by evaporation of the solvent under reduced pressure.

The residue was dissolved in 60 ml of methanol and 200 mg of 5% palladium hydroxide/carbon was added thereto. Then hydrogenation was performed under stirring for 3 hours. The catalyst was filtered off and the solvent was evaporated under reduced pressure. The residue was dissolved in 60 ml of ethyl acetate and 5.20 ml of a 4N solution of hydrogen chloride in ethyl acetate was added thereto. After evaporation of the solvent under reduced pressure, the crystals thus precipitated were recrystallized from ethyl acetate to give 4.77 g of N,N-di-n-propyl-2-[4-hydroxy-3-(2-phenylethoxy)phenyl] ethylamine hydrochloride. m.p. 124°–125° C.

By using the corresponding starting materials, the substantially same procedure as the above was performed to thereby give the following compounds.

N,N-Di-n-propyl-2-[3-hydroxy-4-(2-phenylethoxy)phenyl] ethylamine hydrochloride.

m.p. 123°–124° C. (recrystallized from ethyl acetate).

N,N-Di-n-propyl-2-[3-hydroxy-4-methoxy-5-(2-phenylethoxy)phenyl] ethylamine hydrochloride.

m.p. 151°–153.5° C. (recrystallized from dichloromethane/ethyl acetate).

N,N-Di-n-propyl-2-[3-[2-(4-hydroxyphenyl)ethoxy]-4-methoxyphenyl] ethylamine hydrochloride.

NMR (CDCl$_3$) δ (ppm); 1.00 (6H, t, J=7.4 Hz), 1.75°–1.98 (4H, m), 2.78–3.09 (10H, m), 3.83 (3H, s), 4.23 (2H, t, J=6.3 Hz), 6.10 (1H, d, J=1.8 Hz), 6.62 (1H, dd, J=1.8, 8.2 Hz), 6.75 (1H, d, J=8.2 Hz), 6.91 (2H, d, J=8.4 Hz), 7.08 (2H, d, J=8.4 Hz), 7.55 (1H, brs, exchangeable with D$_2$O), 11.62 (1H, brs, exchangeable with D$_2$O).

MS m/e; 372 (M$^+$+1).

EXAMPLE 16

Production of
N-n-hexyl-N-n-propyl-2-[4-methoxy-3-(2-phenylethoxy] phenyl]ethylamine Hydrochloride 432 mg of N-n-propyl-2-[4-methoxy-3-(2-phenylethoxy)phenyl] ethylamine hydrochloride, 0.87 ml of 1-bromo-n-hexane and 379 mg of anhydrous potassium carbonate were stirred in 4.4 ml of N,N-dimethylformamide at room temperature for 2 days. The reaction mixture was poured into water and extracted with ethyl acetate. The organic layer was successively washed with water and a saturated aqueous solution of sodium chloride, dried over anhydrous magnesium sulfate and filtered, followed by evaporation of the solvent under reduced pressure. The residue was subjected to silica gel chromatography (developing solvent; n-hexane:ethyl acetate=1:1). The target fraction was concentrated and dissolved in 2 ml of ethyl acetate. After adding 0.25 ml of a 4N solution of hydrogen chloride in ethyl acetate, the solvent was evaporated to give 358 mg of oily N-n-hexyl-N-n-propyl- 2-[4-methoxy-3-(2-phenylethoxy)phenyl]ethylamine hydrochloride.

NMR (CDCl$_3$) δ (ppm); 0.89 (3H, t, J=6.5 Hz), 1.00 (3H, t, J=7.4 Hz), 1.24–1.37 (6H, m), 1.68–1.93 (4H, m), 2.92–3.08 (4H, m), 3.11 (4H, m), 3.16 (2H, t, J=7.5 Hz), 3.84 (3H, s), 4.20 (2H, t, J=7.5 Hz), 6.72–6.84 (3H, m), 7.21–7.38 (5H, m), 12.34 (1H, brs, exchangeable with D$_2$O).

MS m/e; 398 (M$^+$+1).

By using the corresponding starting compounds in place of the 1-bromo-n-hexane, a procedure substantially the same as the above was performed to give the following compounds.

N-Isoamyl-N-n-propyl-2-[4-methoxy-3-(2-phenylethoxy)phenyl]ethylamine hydrochloride.

NMR (CDCl$_3$) δ (ppm); 0.95 (6H, d, J=6.4 Hz), 1.00 (3H, t, J=7.5 Hz), 1.57–1.76 (3H, m), 1.96–1.94 (2H, m), 2.91–3.08 (4H, m), 3.11 (4H, brs), 3.16 (2H, t, J=7.5 Hz), 3.84 (3H, s), 4.20 (2H, t, J=7.5 Hz), 6.73–6.85 (3H, m), 7.21–7.38 (5H, m), 12.35 (1H, brs, exchangeable with D$_2$O).

MS m/e; 384 (M$^+$+1).

N-(2-Ethoxycarbonylethyl)-N-n-propyl-2-[4-methoxy-3-(2-phenylethoxy)phenyl] ethylamine.

NMR (CDCl$_3$) δ (ppm); 0.88 (3H, t, J=7.5 Hz), 1.24 (3H, t, J=7.5 Hz), 1.48 (2H, m), 2.46 (4H, brt, J=7.5 Hz), 2.66 (4H, brs), 2.85 (2H, t, J=7.5 Hz), 3.16 (2H, t, J=7.5 Hz), 3.83 (3H, s), 4.09 (2H, t, J=7.5 Hz), 4.18 (2H, q, J=7.5 Hz), 6.65–6.83 (3H, m), 7.15–7.38 (5H, m).

MS m/e; 413 (M⁺).
N-(2-Hydroxycarbonylethyl)-N-n-propyl-2-[4-methoxy-3-(2-phenylethoxy)phenyl] ethylamine hydrochloride.
m.p. 99°–102° C. (recrystallized from dichloromethane/isopropyl ether).
N-(3-Hydroxypropyl)-N-n-propyl-2-[4-methoxy-3-(2-phenylethoxy)phenyl] ethylamine hydrochloride.
m.p. 91°–92° C. (recrystallized from isopropanol).

TEST EXAMPLE 1

Receptor Binding Experiment

As test animals, male Wistar rats were used.

As a [$^3$H]-labeled ligand, (+)[$^3$H]3-PPP [3-(3-hydroxyphenyl)-N-n-propylpiperidine] was used for sigma receptor, while (−)[$^3$H] sulpiride was used for D$_2$ receptor.

Binding reactions with the use of these [$^3$H]-labeled ligands were performed respectively in accordance with the following methods (1) and (2) described in Molecular Pharmacology, 32, p. 772 (1987) and Journal of Pharmacy and Pharmacology, 32, p. 820 (1987).

(1) (+) [$^3$H] 3-PPP binding: A membrane preparation obtained from the whole brain of rat, (+) [$^3$H] 3-PPP and a test drug were reacted in a 50 mM Tris hydrochloride buffer (pH 8.0) at 21° C. for 90 minutes.

(2) (−) [$^3$H] sulpiride binding: A membrane preparation obtained from the corpus striatum of rat, (−) [$^3$H] sulpiride and a test drug were reacted in a 50 mM Tris hydrochloride buffer (pH 7.7) at 37° C. for 10 minutes.

After the completion of each reaction, the reaction mixture was filtered under sucking onto a glass filter (GF/B) and the radioactivity of the filter paper was measured with a liquid scintillation spectrometer.

The data obtained by reacting in the presence of 10 μM (+) 3-PPP and 10 μM (−) thiapride were regarded respectively as the nonspecific binding of (+) [$^3$H] 3-PPP and (−) [$^3$H] sulpiride. Then the difference between the total binding and the nonspecific binding was referred to as the specific binding. The [$^3$H]-labeled ligand at a definite concentration and the test drug at various concentrations were reacted under the conditions as specified in the above (1) or (2) to thereby give an inhibition curve. From this inhibition curve, the 50% inhibitory concentration of the test drug on each binding (IC$_{50}$) was determined. Table 1 shows the results.

TABLE 1

| Test drug | Sigma (nM) | D$_2$ (nM) |
|---|---|---|
| A | 7.21 | 112 |
| B | 28.9 | >1000 |
| C | 26.4 | >1000 |
| D | 17.9 | 1450 |
| E | 11.1 | 169 |
| F | 10.9 | 438 |
| G | 13.3 | 1910 |
| H | 21.6 | 3520 |
| I | 1.29 | >1000 |
| J | 0.984 | 950 |
| K | 4.70 | >1000 |
| L | 33.0 | 183 |
| M | 3.09 | 2500 |
| N | 1.03 | >10000 |
| O | 1.49 | 6600 |
| P | 1.03 | 4990 |
| Q | 9.35 | >10000 |
| R | 11.5 | >10000 |
| S | 18.5 | >10000 |
| T | 2.71 | >10000 |

TABLE 1-continued

| Test drug | Sigma (nM) | D$_2$ (nM) |
|---|---|---|
| U | 12.5 | >1000 |
| V | 1.65 | >1000 |
| W | 28.3 | 5350 |
| X | 7.06 | 791 |
| Y | 6.60 | 2350 |
| Z | 6.83 | 9180 |
| 3-PPP | 24.3 | — |
| Rimcazole | 1640 | 86000 |
| AA | 94.4 | 40800 |

(Note 1)

A; N,N-Di-n-propyl-2-[5-chloro-2-(2-phenylethoxy)phenyl]ethylamine oxalate.
B; N,N-Di-n-propyl-3-[5-chloro-2-(2-phenylethoxy)phenyl]propylamine oxalate.
C; N,N-Di-n-propyl-4-[5-chloro-2-(2-phenylethoxy)phenyl]butylamine oxalate.
D; N,N-Di-n-propyl-2-[4-chloro-2-(2-phenylethoxy)phenyl]ethylamine hydrochloride.
E; N,N-Di-n-propyl-2-[5-bromo-2-(2-phenylethoxy)phenyl]ethylamine oxalate.
F; N,N-Di-n-propyl-3-[5-bromo-2-(2-phenylethoxy)phenyl]propylamine oxalate.
G; N,N-Di-n-propyl-2-[5-fluoro-2-(2-phenylethoxy)phenyl]ethylamine hydrochloride.
H; N,N-Di-n-propyl-2-[3-fluoro-2-(2-phenylethoxy)phenyl]ethylamine oxalate.
I; N,N-Di-n-propyl-2-[4-methoxy-3-(2-phenylethoxy)phenyl]ethylamine oxalate.
J; N,N-Di-n-propyl-3-[4-methoxy-3-(2-phenylethoxy)phenyl]propylamine oxalate.
K; N,N-Di-n-propyl-2-[4-methoxy-3-(3-phenylpropoxy)phenyl]ethylamine oxalate.
L; N-2-[4-Methoxy-3-(2-phenylethoxy)phenyl]ethyl-N'-phenylpiperazine oxalate.
M; N,N-Di-n-propyl-2-[4-hydroxy-3-(2-phenylethoxy)phenyl]ethylamine hydrochloride.
N; N,N-Di-n-propyl-2-[4-methoxy-3-[2-(4-fluorophenyl)ethoxy]phenyl] ethylamine hydrochloride.
O; N,N-Di-n-propyl-2-[4-methoxy-3-[2-(3-chlorophenyl)ethoxy]phenyl] ethylamine oxalate.
P; N,N-Di-n-propyl-2-[4-methoxy-3-[2-(4-methoxyphenyl)ethoxy] phenyl]ethylamine oxalate.
Q; N,N-Di-n-propyl-2-[4-methoxy-3-[2-(2-thienyl)ethoxy] phenyl] ethylamine hydrochloride.
R; N,N-Di-n-propyl-2-[3-methoxy-4-(2-phenylethoxy)phenyl]ethylamine oxalate.
S; N-n-propyl-N-3-hydroxypropyl-2-[4-methoxy-3-(2-phenylethoxy)phenyl] ethylamine oxalate.
T; N,N-Di-n-propyl-2-[3-methoxy-2-(2-phenylethoxy)phenyl]ethylamine oxalate.
U; N,N-Di-n-propyl-3-[3-methoxy-2-(2-phenylethoxy)phenyl]propylamine oxalate.
V; N,N-Di-n-propyl-2-[3-methoxy-2-(3-phenylpropoxy)phenyl]ethylamine oxalate.
W; N-2-[3-Methoxy-2-(2-phenylethoxy)phenyl]ethylpyrrolidine oxalate.
X; N,N-Di-n-propyl-2-[5-methoxy-2-(2-phenylethoxy)phenyl]ethylamine hydrochloride.
Y; N,N-Di-n-propyl-2-[4-methoxy-2-(2-phenylethoxy)phenyl]ethylamine oxalate.
Z; N,N-Di-n-propyl-2-[2-methoxy-4-(2-phenylethoxy)phenyl]ethylamine oxalate.

(Note 2)

Regarding Rimcazole, the data given in European Journal of Pharmacology, 155, p. 345 (1988) are quoted. The data of $D_2$ receptor are expressed as the value obtained from spiperone binding.

AA means N,N-dimethyl-2-(4-methoxy-3-benzyloxyphenyl)ethylamine hydrochloride (m.p. 154°–155° C., recrystallized from isopropanol) which was synthesized by the method described in J. C. S. Perkin I. (1975), p. 1140 and converted into hydrochloride by treating with hydrogen chloride in isopropanol.

TEST EXAMPLE 2

Examination on Antagonism Against (+) SKF 10047-induced Abnormal Behaviors (1) Dose The present compounds I, J and T were orally administered each in doses of 0.001, 0.01 and 0.1 mg/kg. Preparations were formulated by dissolving 10 mg of each test drug in 1 ml of dimethylsulfoxide, diluting with physiological saline to a concentration of 0.1 mg/kg, and further diluting the obtained solution to 0.01 and 0.001 mg/kg (administration dose: 0.1 ml per 10 g body weight of mouse).

The invention compound A, the comparative drug AA and Rimcazole were each orally administered in doses of 0.03, 0.1, 0.3, 1.0, 3.0 and 10.0 mg/kg. Preparations were formulated by suspending in a 5% solution of acacia.

(+) SKF10047 [(+)-N-allylnormetazocine hydrochloride; manufactured by Sigma] was intraperitoneally administered in a dose of 30 mg/kg. The preparation was formulated by dissolving in physiological saline.

(2) Test Method

As test animals, ICR male mice (Nippon Charles River) aged 4 to 5 weeks were used. Each group had 10 animals.

Each animal was introduced into a transparent acrylic resin cage (24 cm in length×17.5 cm in width×12 cm in height) and allowed to fully adapt to the environment. 35 minutes after the administration of a preparation of a test drug, (+) SKF10047 was administered. From 10 minutes thereafter, the stereotypy scores [listed in Table 2, Synapse, 2, p. 240 (1988)] were evaluated for 40 minutes at intervals of 5 minutes and the $ED_{25}$ (mg/kg) was determined. Table 3 shows the results.

TABLE 2

| Score | Stereotypy |
|---|---|
| 0 | Normal behavior. |
| 1 | Sniffing, grooming, standing up. |
| 2 | Losing the balance, falling over immediately after standing up, sniffing more strongly than 1. |
| 3 | Spinning round, walking backward. |
| 4 | Continuously spinning round, rolling, walking backward. |
| 5 | Bending the limbs, head and neck, while stretching the body. |

TABLE 3

| Test drug | $ED_{25}$ (mg/kg) |
|---|---|
| A | 0.235 |
| I | 0.0008 |
| J | 0.00263 |
| T | 0.0017 |

TABLE 3-continued

| Test drug | $ED_{25}$ (mg/kg) |
|---|---|
| AA | 23.6 |
| Rimcazole | 37.0 |

(Note 1)

A; N,N-Di-n-propyl-2-[5-chloro-2-(2-phenylethoxy)phenyl]ethylamine oxalate.
I; N,N-Di-n-propyl-2-[4-methoxy-3-(2-phenylethoxy)phenyl]ethylamine oxalate.
J; N,N-Di-n-propyl-3-[4-methoxy-3-(2-phenylethoxy)phenyl]propylamine oxalate.
T; N,N-Di-n-propyl-2-[3-methoxy-2-(2-phenylethoxy)phenyl]ethylamine oxalate.

(Note 2)

AA means N,N-dimethyl-2-(4-methoxy-3-benzyloxyphenyl)ethylamine hydrochloride (m.p. 154°–155° C., recrystallized from isopropanol) which was synthesized by the method described in J. C. S. Perkin I. (1975), p. 1140 and converted into hydrochloride by treating with hydrogen chloride in isopropanol.

As Rimcazole, a product of Aldrich Chemical Co., Inc. was used.

INDUSTRIAL APPLICABILITY

The compound of the present invention shows a specific and high affinity for sigma receptor. Therefore, the compound of the present invention, which exhibits a antipsychotic actin without causing any extrapyramidal disorders, is useful as a remedy for schizophrenia as well as a remedy for abnormal behaviors accompanying cerebrovascular disorders and senile dementia.

We claim:

1. An alkoxyphenylalkylamine derivative represented by the following formula:

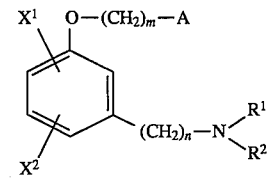

wherein $X^1$ and $X^2$ may be either the same or different from each other and each represents a hydrogen atom, a hydroxyl group, an alkoxy group having 1 to 5 carbon atoms or an alkoxy group having 1 to 5 carbon atoms and substituted with a phenyl group; $R^1$ and $R^2$ may be either the same or different from each other and each represents a hydrogen atom, an alkyl group having 1 to 7 carbon atoms or an alkyl group having 1 to 7 carbon atoms and substituted with a substituent selected from the group consisting of a hydroxyl group, a carboxyl group and an alkoxycarbonyl group at the end, or, $R^1$ and $R^2$ together with the adjacent nitrogen atom represent a pyrrolidino group, a piperidino group, a homopiperidino group, a morpholino group, a piperazino group, a homopiperazino group or a piperazino group substituted with a substituent selected from the group consisting of a phenyl group, a phenyl group substituted with a lower alkyl group or a lower alkoxy group, a pyridyl group, a pyridyl group substituted with a lower alkyl group or a lower alkoxy group, a pyrimidyl group and a pyrimidyl group substituted with a lower alkyl group or a lower alkoxy group; A represents a phenyl group, a phenyl group substituted with 1 to 3 substituents selected from the group consisting of a halogen atom, a hydroxyl group and an alkoxy group having 1 to 5 carbon atoms, or a thienyl group; m is an integer of from 2 to 5; and n is an integer of from 2 to 7, and a salt thereof.

2. N,N-Di-n-propyl-2-[4-methoxy-3-(2-phenylethoxy)phenyl] ethylamine hydrochloride.

3. N,N-Di-n-propyl-3-[4-methoxy-3-(2-phenylethoxy)phenyl] propylamine hydrochloride.

* * * * *